United States Patent
Bergeron, Jr.

(10) Patent No.: US 9,567,309 B2
(45) Date of Patent: *Feb. 14, 2017

(54) DESFERRITHIOCIN POLYETHER ANALOGUES

(71) Applicant: University of Florida Research Foundation, Inc., Gainesville, FL (US)

(72) Inventor: Raymond J. Bergeron, Jr., Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/811,598

(22) Filed: Jul. 28, 2015

(65) Prior Publication Data

US 2015/0336911 A1 Nov. 26, 2015

Related U.S. Application Data

(60) Division of application No. 14/264,959, filed on Apr. 29, 2014, now Pat. No. 9,096,553, which is a continuation of application No. 13/631,025, filed on Sep. 28, 2012, now Pat. No. 8,722,899, which is a continuation of application No. 11/973,001, filed on Oct. 4, 2007, now Pat. No. 8,278,458, which is a continuation of application No. PCT/US2006/010945, filed on Mar. 22, 2006.

(60) Provisional application No. 60/668,045, filed on Apr. 4, 2005.

(51) Int. Cl.
*A61K 31/426* (2006.01)
*C07D 277/12* (2006.01)
*C07D 277/10* (2006.01)

(52) U.S. Cl.
CPC ........... *C07D 277/12* (2013.01); *A61K 31/426* (2013.01); *C07D 277/10* (2013.01); *C07B 2200/07* (2013.01)

(58) Field of Classification Search
CPC .................................................. A61K 31/426
USPC ........................................................ 548/201
See application file for complete search history.

(56) References Cited

U.S. PATENT DOCUMENTS

| | | | |
|---|---|---|---|
| 3,274,207 A | 9/1966 | Kollonitsch |
| 3,809,754 A | 5/1974 | Bertrand |
| 3,882,110 A | 5/1975 | Clemence et al. |
| 4,270,537 A | 6/1981 | Romaine |
| 4,367,233 A | 1/1983 | Clark et al. |
| 4,406,905 A | 9/1983 | Zahner et al. |
| 4,457,935 A | 7/1984 | Iwao et al. |
| 4,457,936 A | 7/1984 | Draeger et al. |
| 4,558,059 A | 12/1985 | Kawasaki et al. |
| 4,596,556 A | 6/1986 | Morrow et al. |
| 4,736,060 A | 4/1988 | Tomuro et al. |
| 4,775,675 A | 10/1988 | Gyorgydeak et al. |
| 4,790,824 A | 12/1988 | Morrow et al. |
| 4,886,499 A | 12/1989 | Cirelli et al. |
| 4,902,700 A | 2/1990 | Hayasi et al. |
| 4,914,208 A | 4/1990 | Jakob et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,084,083 A | 1/1992 | Lewis et al. |
| 5,106,992 A | 4/1992 | Magnin et al. |
| 5,141,496 A | 8/1992 | Dalto et al. |
| 5,169,858 A | 12/1992 | Rubin |
| 5,182,402 A | 1/1993 | Lewis et al. |
| 5,190,521 A | 3/1993 | Hubbard et al. |
| 5,192,781 A | 3/1993 | Bru-Magniez et al. |
| 5,312,335 A | 5/1994 | McKinnon et al. |
| 5,328,483 A | 7/1994 | Jacoby |
| 5,334,144 A | 8/1994 | Alchas et al. |

(Continued)

FOREIGN PATENT DOCUMENTS

| CS | 205217 B1 | 5/1981 |
|---|---|---|
| DE | 2245560 A1 | 3/1974 |

(Continued)

OTHER PUBLICATIONS

Extended European Search Report, mailed Jan. 19, 2010, in connection with Application No. EP 07874513.0.

(Continued)

*Primary Examiner* — Laura L. Stockton
(74) *Attorney, Agent, or Firm* — Wolf, Greenfield & Sacks, P.C.

(57) ABSTRACT

Compounds represented by structural formulas described herein, such as Structural Formula (I):

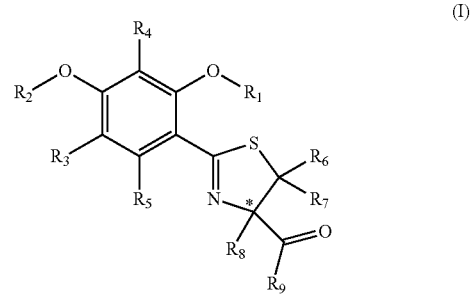

or a pharmaceutically acceptable salt thereof are useful in treating conditions such as metal overload, oxidative stress, and neoplastic and preneoplastic conditions.

26 Claims, 9 Drawing Sheets

(56) References Cited

U.S. PATENT DOCUMENTS

| | | |
|---|---|---|
| 5,339,163 A | 8/1994 | Homma et al. |
| 5,383,851 A | 1/1995 | McKinnon, Jr. et al. |
| 5,385,922 A | 1/1995 | Bron et al. |
| 5,393,777 A | 2/1995 | Crosa |
| 5,417,662 A | 5/1995 | Hjertman et al. |
| 5,442,073 A | 8/1995 | Eicken et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,614,520 A | 3/1997 | Kondo et al. |
| 5,649,912 A | 7/1997 | Peterson |
| 5,704,911 A | 1/1998 | Parsons |
| 5,840,739 A | 11/1998 | Bergeron, Jr. |
| 5,893,397 A | 4/1999 | Peterson et al. |
| 5,993,412 A | 11/1999 | Deily et al. |
| 6,080,764 A | 6/2000 | Chihiro et al. |
| 6,083,966 A | 7/2000 | Bergeron, Jr. |
| 6,147,070 A | 11/2000 | Facchini |
| 6,159,983 A | 12/2000 | Bergeron, Jr. |
| 6,251,927 B1 | 6/2001 | Lai et al. |
| 6,373,912 B1 | 4/2002 | Yu |
| 6,437,143 B2 | 8/2002 | Moinet et al. |
| 6,521,652 B1 | 2/2003 | Bergeron |
| 6,525,080 B1 | 2/2003 | Bergeron |
| 6,559,315 B1 | 5/2003 | Bergeron |
| 6,864,270 B2 | 3/2005 | Bergeron, Jr. |
| RE39,132 E | 6/2006 | Bergeron, Jr. |
| 7,126,004 B2 | 10/2006 | Bergeron |
| 7,144,904 B2 | 12/2006 | Bergeron, Jr. |
| 7,531,563 B2 | 5/2009 | Bergeron |
| 8,008,502 B2 | 8/2011 | Bergeron |
| 8,063,227 B2 | 11/2011 | Tapper et al. |
| 8,278,458 B2 | 10/2012 | Bergeron, Jr. |
| 8,324,397 B2 | 12/2012 | Bergeron, Jr. |
| 8,604,216 B2 | 12/2013 | Bergeron, Jr. |
| 8,722,899 B2 | 5/2014 | Bergeron, Jr. |
| 9,096,553 B2 * | 8/2015 | Bergeron, Jr. ........ C07D 277/10 |
| 9,174,948 B2 | 11/2015 | Bergeron, Jr. |
| 2002/0049316 A1 | 4/2002 | Halbert et al. |
| 2003/0083349 A1 | 5/2003 | Bergeron, Jr. |
| 2003/0236417 A1 | 12/2003 | Bergeron |
| 2004/0044220 A1 | 3/2004 | Bergeron, Jr. |
| 2004/0132789 A1 | 7/2004 | Bergeron, Jr. |
| 2005/0033057 A1 | 2/2005 | Bergeron |
| 2005/0234113 A1 | 10/2005 | Bergeron, Jr. |
| 2006/0211746 A1 | 9/2006 | Bergeron, Jr. |
| 2007/0238767 A1 | 10/2007 | Bergeron |
| 2008/0214630 A1 | 9/2008 | Bergeron |
| 2010/0093812 A1 | 4/2010 | Bergeron, Jr. |
| 2010/0094016 A1 | 4/2010 | Bergeron |
| 2010/0137346 A1 | 6/2010 | Bergeron, Jr. |
| 2010/0137383 A1 | 6/2010 | Tapper et al. |
| 2011/0053993 A1 | 3/2011 | McCall, Jr. et al. |
| 2011/0275636 A1 | 11/2011 | Malecha |
| 2012/0184586 A1 | 7/2012 | Bergeron, Jr. |
| 2013/0030028 A1 | 1/2013 | Bergeron, Jr. |
| 2013/0210870 A1 | 8/2013 | Bergeron, Jr. |
| 2014/0235680 A1 | 8/2014 | Bergeron, Jr. |
| 2014/0323534 A1 | 10/2014 | Bergeron, Jr. |
| 2014/0343110 A1 | 11/2014 | Bergeron, Jr. |
| 2016/0022645 A1 * | 1/2016 | Bergeron, Jr. ........ A61K 31/426 514/365 |

FOREIGN PATENT DOCUMENTS

| | | |
|---|---|---|
| DE | 3002989 A1 | 7/1981 |
| EP | 0 214 101 A2 | 3/1987 |
| EP | 0 214 933 A2 | 3/1987 |
| EP | 0 325 559 A2 | 7/1989 |
| EP | 0 513 379 A1 | 11/1992 |
| EP | 2062581 A1 | 5/2009 |
| FR | 2247243 A2 | 5/1975 |
| GB | 1292170 A | 10/1972 |
| GB | 1320534 A | 6/1973 |
| GB | 1382887 A | 2/1975 |
| JP | 57-058682 A | 4/1982 |
| WO | WO 94/11367 A1 | 5/1994 |
| WO | WO 97/13537 A1 | 4/1997 |
| WO | WO 97/36885 A1 | 10/1997 |
| WO | WO 97/37705 A1 | 10/1997 |
| WO | WO 99/34850 A1 | 7/1999 |
| WO | WO 99/53039 A1 | 10/1999 |
| WO | WO 00/12493 A1 | 3/2000 |
| WO | WO 00/16763 A2 | 3/2000 |
| WO | WO 01/27119 A2 | 4/2001 |
| WO | WO 03/078467 A1 | 9/2003 |
| WO | WO 2004/017959 A2 | 3/2004 |
| WO | WO 2005/023310 A2 | 3/2005 |
| WO | WO 2005/034949 A1 | 4/2005 |
| WO | WO 2006/055412 A1 | 5/2006 |
| WO | WO 2006/107626 A1 | 10/2006 |
| WO | WO 2008/115433 A1 | 9/2008 |
| WO | WO 2008/130395 A2 | 10/2008 |
| WO | WO 2009/053628 A2 | 4/2009 |
| WO | WO 2010/009120 A2 | 1/2010 |
| WO | WO 2011/017054 A2 | 2/2011 |
| WO | WO 2011/028255 A2 | 3/2011 |
| WO | WO 2012/027794 A2 | 3/2012 |
| WO | WO 2013/090750 A1 | 6/2013 |
| WO | WO 2013/090766 A1 | 6/2013 |
| WO | WO 2014/134701 A1 | 9/2014 |

OTHER PUBLICATIONS

International Search Report and Written Opinion, mailed Jan. 8, 2009, in connection with Application No. PCT/US2007/025377.

International Preliminary Report on Patentability, mailed Jun. 23, 2009, in connection with Application No. PCT/US2007/025377.

Extended European Search Report, mailed Dec. 27, 2010, in connection with Application No. EP 08742093.1.

International Search Report and Written Opinion, mailed Jun. 19, 2008, in connection with Application No. PCT/US2008/003433.

International Preliminary Report on Patentability, mailed Sep. 24, 2009, in connection with Application No. PCT/US2008/003433.

International Search Report and Written Opinion, mailed May 23, 2011, in connection with Application No. PCT/US2010/002336.

International Preliminary Report on Patentability, mailed Mar. 8, 2012, in connection with Application No. PCT/US2010/002336.

International Search Report and Written Opinion, mailed Mar. 5, 2004, in connection with Application No. PCT/US2003/028304.

International Search Report and Written Opinion, mailed Aug. 9, 2006, in connection with Application No. PCT/US2006/010945.

International Preliminary Report on Patentability, mailed Oct. 18, 2007, in connection with Application No. PCT/US2006/010945.

Supplementary European Search Report, mailed Dec. 5, 2001, in connection with Application No. EP 99945267.5.

International Search Report, mailed Jan. 19, 2000, in connection with Application No. PCT/US1999/019691.

Written Opinion, mailed Aug. 21, 2000, in connection with Application No. PCT/US1999/019691.

International Preliminary Examination Report, mailed Feb. 2, 2001, in connection with Application No. PCT/US1999/019691.

Extended European Search Report, mailed Mar. 25, 2013, in connection with Application No. EP 10814064.1.

International Search Report and Written Opinion, mailed Apr. 19, 2013, in connection with Application No. PCT/US2012/069795.

International Search Report and Written Opinion, mailed Apr. 12, 2013, in connection with Application No. PCT/US2012/069826.

International Preliminary Report on Patentability, mailed Jun. 26, 2014, in connection with Application No. PCT/US2012/069795.

International Preliminary Report on Patentability, mailed Jun. 26, 2014, in connection with Application No. PCT/US2012/069826.

Invitation to Pay Additional Fees, mailed Jan. 27, 2015, in connection with Application No. PCT/US2014/066961.

(56) References Cited

OTHER PUBLICATIONS

Invitation to Pay Additional Fees, mailed Jan. 27, 2015, in connection with Application No. PCT/US2014/066965.
European Search Report, mailed Mar. 20, 2015, in connection with Application No. EP 12857135.3.
International Search Report and Written Opinion, mailed Apr. 14, 2015, in connection with Application No. PCT/US2014/066961.
International Search Report and Written Opinion, mailed Apr. 14, 2015, in connection with Application No. PCT/US2014/066965.
Extended European Search Report, mailed Jul. 9, 2015, in connection with Application No. EP 12857135.3.
[No Author Listed] Highlights of Prescribing Information: EXJADE. Novartis Pharma Stein AG. 2010. Available at http://www.pharma.us.novartis.com/product/pi/pdf/exjade.pdf. Last accessed Sep. 9, 2010. 14 pages.
[No Author Listed] "Ion exchanger." Ullmanns Encyclopedia of Industrial Chemistry. 5th Ed. vol. 14A:446-56.
[No Author Listed] Databse CHEMCATS, Accession No. 2003:2524667; TimTec Overseas Stock; May 19, 2003.
[No Author Listed] Desferal. Product Information. Novartis Pharmaceuticals Corporation. East Hanover, NJ. 2011. Available at www.pharma.us.novartis.com/product/pi/pdf/desferal.pdf. Last accessed Jan. 25, 2013.
[No Author Listed], Closed head injury. Wikipedia. http://en.wikipedia.org/wild/Close_head_injury [last accessed Nov. 28, 2011]. 7 pages.
[No Author Listed], Irritable bowel syndrome. Wikipedia. http://en.wikipedia.org/wiki/Irritable_bowel_syndrome [last accessed Nov. 28, 2011]. 24 pages.
[No Author Listed], Macular degeneration. Wikipedia. http://en.wikipedia.org/wiki/Macular_degeneration [last accessed Nov. 28, 2011]. 14 pages.
[No Author Listed], Reperfusion injury. Wikipedia. http://en.wikipedia.org/wild/Reperfusion_injury [last accessed Nov. 28, 2011]. 7 pages.
[No Author Listed], Stroke. Wikipedia. http://en.wikipedia.org/wiki/Stroke [last accessed Nov. 28, 2011]. 29 pages.
Allgayer, Clinical relevance of oxygen radicals in inflammatory bowel disease—facts and fashion. Klin Wochenschr. Dec. 15, 1991;69(21-23):1001-3.
Al-Refaie et al., Zinc concentration in patients with iron overload receiving oral iron chelator 1,2-dimethyl-3-hydroxypyrid-4-one or desferrioxamine. J Clin Pathol. 1994;47:657-60.
Anderegg et al., Metal Complex Formation of a New Siderophore Desferrithiocin and of Three Related Ligands. J Chem Soc Chem Commun. 1990:1194-6.
Angelucci et al., Hepatic iron concentration and total body iron stores in thalassemia major. N Engl J Med. Aug. 3, 2000;343(5):327-31.
Babbs et al., Oxygen radicals in ulcerative colitis. Free Radic Biol Med. 1992;13(2):169-81.
Bailly et al., Shedding of kidney injury molecule-1, a putative adhesion protein involved in renal regeneration. J Biol Chem. Oct. 18, 2002;277(42):39739-48. Epub Jul. 23, 2002.
Bartakke et al., Effect of Deferiprone on Urinary Zinc Excretion in Multiply Transfused Children with Thalassemia Major. Ind Ped. Feb. 17, 2005;42:150-4.
Berge et al., Pharmaceutical salts. J Pharm Sci. Jan. 1977;66(1):1-19.
Bergeron et al., (S)-4,5-dihydro-2-(2-hydroxy-4-hydroxyphenyl)-4-methyl-4-thiazolecarboxylic acid polyethers: a solution to nephrotoxicity. J Med Chem. May 4, 2006;49(9):2772-83, published online Apr. 4, 2006.
Bergeron et al., A comparative evaluation of iron clearance models. Ann N Y Acad Sci. 1990;612:378-93.
Bergeron et al., A comparative study of the iron-clearing properties of desferrithiocin analogues with desferrioxamine B in a Cebus monkey model. Blood. Apr. 15, 1993;81(8):2166-73.
Bergeron et al., A comparison of the iron-clearing properties of 1,2-dimethyl-3-hydroxypyrid-4-one, 1,2-diethyl-3-hydroxypyrid-4-one, and deferoxamine. Blood. Apr. 1, 1992;79(7):1882-90.
Bergeron et al., An investigation of desferrithiocin metabolism. J Med Chem. Sep. 2, 1994;37(18):2889-95.
Bergeron et al., Comparison of iron chelator efficacy in iron-overloaded beagle dogs and monkeys (Cebus apella). Comp Med. Dec. 2004;54(6):664-72.
Bergeron et al., Desazadesmethyldesferrithiocin Analogues as Orally Effective Iron Chelators. J Med Chem. 1999;42:95-108.
Bergeron et al., Desferrithiocin analogue based hexacoordinate iron(III) chelators. J Med Chem. Jan. 2, 2003;46(1):16-24.
Bergeron et al., Desferrithiocin analogue iron chelators: iron clearing efficiency, tissue distribution, and renal toxicity. Biometals. Apr. 2011;24(2):239-58. Epub Nov. 20, 2010.
Bergeron et al., Desferrithiocin analogue uranium decorporation agents. Int J Radiat Biol. Apr. 2009;85(4):348-61.
Bergeron et al., Desferrithiocin analogues and nephrotoxicity. J Med Chem. Oct. 9, 2008;51(19):5993-6004. Epub Sep. 13, 2008.
Bergeron et al., Design, synthesis, and testing of non-nephrotoxic desazadesferrithiocin polyether analogues. J Med Chem. Jul. 10, 2008;51(13):3913-23. Epub Jun. 6, 2008.
Bergeron et al., Design, Synthesis, and Testing of Polyamine Vectored Iron Chelators. Synthesis (Stuttg). 2010;2010(21):3631-3636.
Bergeron et al., Effects of C-4 stereochemistry and C-4' hydroxylation on the iron clearing efficiency and toxicity of desferrithiocin analogues. J Med Chem. Jul. 1, 1999;42(13):2432-40.
Bergeron et al., Evaluation of desferrithiocin and its synthetic analogues as orally effective iron chelators. J Med Chem. Jul. 1991;34(7):2072-8.
Bergeron et al., Evaluation of the desferrithiocin pharmacophore as a vector for hydroxamates. J Med Chem. Jul. 29, 1999;42(15):2881-6.
Bergeron et al., HBED: A Potential Alternative to Deferoxamine for Iron-Chelating Therapy. Blood. 1998;91:1446-52.
Bergeron et al., Impact of the 3,6,9-Trioxadecyloxy Group on Desazadesferrithiocin Analogue Iron Clearance and Organ Distribution. J Med Chem. Jul. 12, 2007;50(14):3302-13. Epub Jun. 12, 2007.
Bergeron et al., Impact of the Lipophilicity of Desferrithiocin Analogues on Iron Clearance. Medicinal Inorg Chem. 2005:366-83.
Bergeron et al., Influence of iron on in vivo proliferation and lethality of L1210 cells. J Nutr. Mar. 1985;115(3):369-74.
Bergeron et al., Iron chelation promoted by desazadesferrithiocin analogs: An enantioselective barrier. Chirality. Aug. 2003;15(7):593-9.
Bergeron et al., Iron Chelators and Therapeutic Uses. In: Burger's Medicinal Chemistry, 6th ed. 2003:479-561.
Bergeron et al., Metabolism and pharmacokinetics of N1,N11-diethylnorspermine in a Cebus apella primate model. Cancer Res. Aug. 15, 2000;60(16):4433-9.
Bergeron et al., Metabolism and pharmacokinetics of N1,N14-diethylhomospermine. Drug Metab Dispos. Mar. 1996;24(3):334-43.
Bergeron et al., Methoxylation of desazadesferrithiocin analogues: enhanced iron clearing efficiency. J Med Chem. Apr. 10, 2003;46(8):1470-7.
Bergeron et al., Partition-variant desferrithiocin analogues: organ targeting and increased iron clearance. J Med Chem. Feb. 10, 2005;48(3):821-31.
Bergeron et al., Pharmacokinetics of orally administered desferrithiocin analogs in cebus apella primates. Drug Metab Dispos. Dec. 1999;27(12):1496-8.
Bergeron et al., Polyamine-vectored iron chelators: the role of charge. J Med Chem. Jun. 16, 2005;48(12):4120-37.
Bergeron et al., Prevention of acetic acid-induced colitis by desferrithiocin analogs in a rat model. Dig Dis Sci. Feb. 2003;48(2):399-407.
Bergeron et al., Structure-activity relationships among desazadesferrithiocin analogues. In: Iron Chelation Therapy. Hershko, ed. 2002:167-84.

(56) References Cited

OTHER PUBLICATIONS

Bergeron et al., Substituent effects on desferrithiocin and desferrithiocin analogue iron-clearing and toxicity profiles. J Med Chem. Aug. 23, 2012;55(16):7090-103. doi: 10.1021/jm300509y. Epub Aug. 13, 2012.

Bergeron et al., Synthesis and biological evaluation of hydroxamate-based iron chelators. J Med Chem. Nov. 1991;34(11):3182-7.

Bergeron et al., Synthesis and biological evaluation of naphthyldesferrithiocin iron chelators. J Med Chem. Apr. 12, 1996;39(8):1575-81.

Bergeron et al., Synthesis of heterobactins A and B and Nocardia heterobactin. Tetrahedron. 2011;67(18):3163-69.

Bergeron et al., The desferrithiocin pharmacophore. J Med Chem. May 13, 1994;37(10):1411-7.

Bergeron et al., The design, synthesis, and evaluation of organ-specific iron chelators. J Med Chem. Nov. 30, 2006;49(24):7032-43, published online Nov. 7, 2006.

Bergeron et al., The impact of polyether chain length on the iron clearing efficiency and physiochemical properties of desferrithiocin analogues. J Med Chem. Apr. 8, 2010;53(7):2843-53.

Bergeron et al., The origin of the differences in (R)- and (S)-desmethyldesferrithiocin. Iron-clearing properties. Ann N Y Acad Sci. Jun. 30, 1998;850:202-16.

Bergeron et al., Vibriobactin antibodies: a vaccine strategy. J Med Chem. Jun. 25, 2009;52(12):3801-13.

Bergeron, Desferrithiocin Polyether Analogue Uranium Decorporation Agents. Quad Chart and White Paper. Research Area #4 Radiological/Nuclear Threat Medical Countermeasures. BARDA CBRN BAA-11-100-SOL-00009. Oct. 27, 2011. 17 pages.

Bergeron, Iron: A Controlling Nutrient in Proliferative Processes. Trends in Biochem Sci. 1986;11:133-36.

Bickel et al., [Metabolic Properties of Actinomycetes.] Ferrioxamine B. Helv Chim Acta. 1960;43:2129-38. German.

Bierer et al., The effect of desferrithiocin, an oral iron chelator, on T-cell function. Blood. Nov. 15, 1990;76(10):2052-9.

Bonkovsky et al., Iron-induced liver injury. Clin Liver Dis. May 2000;4(2):409-29, vi-vii.

Bonventre, Kidney injury molecule-1 (KIM-1): a urinary biomarker and much more. Nephrol Dial Transplant. Nov. 2009;24(11):3265-8. doi: 10.1093/ndt/gfp010. Epub Mar. 23, 2009.

Brittenham et al., Efficacy of deferoxamine in preventing complications of iron overload in patients with thalassemia major. N Engl J Med. Sep. 1, 1994;331(9):567-73.

Brittenham, Disorders of Iron Metabolism: Iron Deficiency and Overload. In: Hermatology: Basic Principles and Practice. 3d Ed. Hoffman et al., eds., Churchill Livingston. New York. 2000:397-428.

Brittenham, Iron chelators and iron toxicity. Alcohol. Jun. 2003;30(2):151-8.

Brittenham, Pyridoxal isonicotinoyl hydrazone. Effective iron chelation after oral administration. Ann N Y Acad Sci. 1990;612:315-26.

Brittenham, Pyridoxal isonicotinoyl hydrazone: an effective iron-chelator after oral administration. Semin Hematol. Apr. 1990;27(2):112-6.

Brunner et al., Carboplatin-containing Porphyrin-platinum Complexes as Cytotoxic and Phototoxic Antitumor Agents. Inorg Chim Acta. 2004;357:4423-51.

Byers et al., Microbial iron transport: iron acquisition by pathogenic microorganisms. Met Ions Biol Syst. 1998;35:37-66.

Caira et al., Crystalline Polymorphism of Organic Compounds. Topics in Current Chemistry. 1998;198:163-208.

Cappellini, Iron-chelating therapy with the new oral agent ICL670 (Exjade). Best Pract Res Clin Haematol. Jun. 2005;18(2):289-98.

Cario, Insulin sensitivity and beta-cell secretion in thalassaemia major with secondary haemochromatosis: assessment by oral glucose tolerance test. Eur J Pediatr. Mar. 2003;162(3):139-46. Epub Jan. 15, 2003.

Conrad et al., Iron absorption and transport. Am J Med Sci. Oct. 1999;318(4):213-29.

Cragg et al., The iron chelator L1 potentiates oxidative DNA damage in iron-loaded liver cells. Blood. Jul. 15, 1998;92(2):632-8.

Dean et al., The Action of Nine Chelators on Iron-Dependent Radical Damage. Free Rad Res. 1994;20(2):83-101.

Domingo et al., Comparative effects of the chelators sodium 4,5-dihydroxybenzene-1,3-disulfonate (Tiron) and diethylenetriaminepentaacetic acid (DTPA) on acute uranium nephrotoxicity in rats. Toxicology. Mar. 14, 1997;118(1):49-59.

Donovan et al., Preclinical and clinical development of deferitrin, a novel, orally available iron chelator. Ann N Y Acad Sci. 2005;1054:492-4.

Dunaief et al., Macular degeneration in a patient with aceruloplasminemia, a disease associated with retinal iron overload. Ophthalmology. Jun. 2005;112(6):1062-5.

Dunaief, Iron induced oxidative damage as a potential factor in age-related macular degeneration: the Cogan Lecture. Invest Ophthalmol Vis Sci. Nov. 2006;47(11):4660-4.

Durbin et al., Chelating agents for uranium(VI): 2. Efficacy and toxicity of tetradentate catecholate and hydroxypyridinonate ligands in mice. Health Phys. May 2000;78(5):511-21.

Durbin et al., In Vivo Chelation of Am(III), Pu(IV), Np(V), and U(VI) in Mice by TREN-(Me-3,2-HOPO). Radiat Prot Dosimetry. 1994;53:305-09.

Durbin, Lauriston S. Taylor Lecture: the quest for therapeutic actinide chelators. Health Phys. Nov. 2008;95(5):465-92.

Farcasiu et al., Geometrical inversion of methoxymethyl cations. J Chem Soc Chem Commun. 1979;24:1124-5.

Farkas et al., Structure-based differences between the metal ion selectivity of two siderophores desferrioxamine B (DFB) and desferricoprogen (DFC): Why DFC is much better Pb(II) sequestering agent than DFB? J Inorg Biochem. 2008;102;1654-9.

Feau et al., Preparation and Optical Properties of Novel 3-Alkoxycarbonyl Aza- and Diazacoumarins. Synth Commun. 2010;40:3033-45.

Fedorak et al., Misoprostol provides a colonic mucosal protective effect during acetic acid-induced colitis in rats. Gastroenterology. Mar. 1990;98(3):615-25.

Finch et al., Ferrokinetics in man. Medicine (Baltimore). Jan. 1970;49(1):17-53.

Finch et al., Iron metabolism. Clin Physiol Biochem. 1986;4(1):5-10.

Finch et al., Perspectives in iron metabolism. N Engl J Med. Jun. 24, 1982;306(25):1520-8.

Fossheim et al., Lanthanide-based susceptibility contrast agents: assessment of the magnetic properties. Magn Reson Med. Feb. 1996;35(2):201-6.

Fritsch et al., Plasmodium falciparum: inhibition in vitro with lactoferrin, desferriferrithiocin, and desferricrocin. Exp Parasitol. Feb. 1987;63(1):1-9.

Fukuda, Chelating agents used for plutonium and uranium removal in radiation emergency medicine. Curr Med Chem. 2005;12(23):2765-70.

Galanello et al., A dose escalation study of the pharmacokinetics, safety & efficacy of deferitrin, an oral iron chelator in beta thalassaemia patients. ASH Annu Meet Abstr. 2007;110: Abstract 2669.

Galanello et al., Safety, tolerability, and pharmacokinetics of ICL670, a new orally active iron-chelating agent in patients with transfusion-dependent iron overload due to beta-thalassemia. J Clin Pharmacol. Jun. 2003;43(6):565-72.

Galey et al., N,N'-bis-(3,4,5-trimethoxybenzyl) ethylenediamine N,N'-diacetic acid as a new iron chelator with potential medicinal applications against oxidative stress. Biochem Pharmacol. Jan. 26, 1996;51(2):103-15.

Ganguly et al., Antiviral activity of isoquinolines carbazoles and other miscellaneous synthetic chemicals in mice. Indian J Med Res. Oct. 1975;63(10):1418-25.

Giardina et al., Chelation therapy in beta-thalassemia: an optimistic update. Semin Hematol. Oct. 2001;38(4):360-6.

Golub et al., Molecular classification of cancer: class discovery and class prediction by gene expression monitoring. Science. Oct. 15, 1999;286(5439):531-7.

(56) References Cited

OTHER PUBLICATIONS

Goodsaid et al., Novel biomarkers of acute kidney toxicity. Clin Pharmacol Ther. Nov. 2009;86(5):490-6. doi: 10.1038/clpt.2009.149. Epub Aug. 26, 2009.
Gorden et al., Rational design of sequestering agents for plutonium and other actinides.Chem Rev. Nov. 2003;103(11):4207-82.
Grady et al., HBED: a potential oral iron chelator. Ann N Y Acad Sci. 1990;612:361-8.
Grady et al., Rhodotorulic acid—investigation of its potential as an iron-chelating drug. J Pharmacol Exp Ther. Jun. 1979;209(3):342-8.
Graf et al., Iron-catalyzed hydroxyl radical formation. Stringent requirement for free iron coordination site. J Biol Chem. Mar. 25, 1984;259(6):3620-4.
Grishman et al., Neutrophil-mediated mucosal injury. Role of reactive oxygen metabolites. Dig Dis Sci. Mar. 1988;33(3 Suppl):6S-15S.
Guilmette et al., Competitive binding of Pu and Am with bone mineral and novel chelating agents. Radiat Prot Dosimetry. 2003;105(1-4):527-34.
Guterman et al., Feasibility of enterochelin as an iron-chelating drug: studies with human serum and a mouse model system. Gen Pharmacol. 1978;9(2):123-7.
Hadziahmetovic et al., The oral iron chelator deferiprone protects against iron overload-induced retinal degeneration. Invest Ophthalmol Vis Sci. Feb. 16, 2011;52(2):959-68. doi: 10.1167/iovs.10-6207.
Hahn et al., Coordination Chemistry of Microbial Iron Transport. 42. Structural and Spectroscopic Characterization of Diastereomeric Cr(III) and Co(III) Complexes of Desferriferrithiocin. J Am Chem Soc. 1990;112:1854-60.
Hallberg, Bioavailability of dietary iron in man. Ann Rev Nutr. 1981;1:123-47.
Halliwell, Free radicals and antioxidants: a personal view. Nutr Rev. Aug. 1994;52(8 Pt 1):253-65.
Halliwell, Iron, Oxidative Damage and Chelating Agents. In: The Development of Iron Chelators for Clinical Use, Bergeron, ed. 1994:33-56.
Han et al., Kidney Injury Molecule-1 (KIM-1): a novel biomarker for human renal proximal tubule injury. Kidney Int. Jul. 2002;62(1):237-44.
Hazen et al., Human neutrophils employ the myeloperoxidase-hydrogen peroxide-chloride system to oxidize alpha-amino acids to a family of reactive aldehydes. Mechanistic studies identifying labile intermediates along the reaction pathway. J Biol Chem. Feb. 27, 1998;273(9):4997-5005.
Henry, Chemotherapeutic nitroheterocycles. Derivatives of 5-nitrothiazole-2-carboxaldehyde and 5-nitrothiazole-2-carboxylic acid. J Med Chem. Mar. 1969;12(2):303-6.
Hoffbrand et al., Long-term trial of deferiprone in 51 transfusion-dependent iron overloaded patients. Blood. Jan. 1, 1998;91(1):295-300.
Hoffbrand, Transfusion Siderosis and Chelation Therapy. Iron in Biochemistry and Medicine. vol. II. London. 1980: 449-527.
Hoffmann et al., Evaluation of a urinary kidney biomarker panel in rat models of acute and subchronic nephrotoxicity. Toxicology. Nov. 9, 2010;277(1-3):49-58. doi: 10.1016/j.tox.2010.08.013. Epub Sep. 9, 2010.
Horackova et al., The antioxidant effects of a novel iron chelator salicylaldehyde isonicotinoyl hydrazone in the prevention of H(2)O(2) injury in adult cardiomyocytes. Cardiovasc Res. Aug. 18, 2000;47(3):529-36.
Hua et al., Long-term effects of experimental intracerebral hemorrhage: the role of iron. J Neurosurg. Feb. 2006;104(2):305-12.
Iranmanesh et al., Chelation of chromium(VI) by combining deferasirox and deferiprone in rats. Biometals. 2013;26:465-71.
Jalal et al., Structure of Anguibactin, a Unique Plasmid-Related Bacterial Siderophore from the Fish Pathogen Vibrio Anguillarum. J Am Chem Soc. 1989;111(1):292-96.

Jarvis et al., Some correlations involving the stability of complexes of transuranium metal ions and ligands with negatively charged oxygen donors. Inorg Chim Acta. 1991;182:229-32.
Kalinowski et al., The evolution of iron chelators for the treatment of iron overload disease and cancer. Pharmacol Rev. Dec. 2005;57(4):547-83.
Kersten et al., Long-term treatment of transfusional iron overload with the oral iron chelator deferiprone (L1): a Dutch multicenter trial. Ann Hematol. Nov. 1996;73(5):247-52.
Kicic et al., The desferrithiocin (DFT) class of iron chelators: potential as antineoplastic agents. Anticancer Drug Des. Aug.-Oct. 2001;16(4-5):195-207.
Kishore et al., Synthesis of α-Poly-[Nε-2-aryl-Δ2-thiazoline-4-carbonyl-L-lysine] with Antival Activity. Ind J Chem. 1977;15B:255-57.
Kitazawa et al., Reduction of ultraviolet light-induced oxidative stress by amino acid-based iron chelators. Biochim Biophys Acta. Dec. 27, 1999;1473(2-3):400-8.
Kitto et al., Post-modification of Helical Dipeptido Polyisocyanides Using the "Click" Reaction. J Mater Chem. 2008;18:5615-24.
Kontoghiorghes et al., 1,2-Dimethyl-3-hydroxypyrid-4-one, an orally active chelator for treatment of iron overload. Lancet. Jun. 6, 1987;1(8545):1294-5.
Kontoghiorghes, New Concepts of Iron and Aluminium Chelation Therapy With Oral L1 (Deferiprone) and Other Chelators. Analyst. Mar. 1995;120:845-51.
Koppenol, Kinetics and Mechanisms of the Fenton Reaction: Implications in Iron Toxicity. In: Iron Chelators: New Development Strategies, Bergeron, ed., 2000:3-10.
Langer et al., Solid complexes with tetravalent metal ions and ethylenediamime tetra-acetic acid (EDTA). J Inorg Nucl Chem. 1964;26:59-72.
Levien et al., Pentetate Calcium Trisodium (Ca-DTPA) and Pentetate Zinc Trisodium (Zn-DTPA). Formulary Drug Reviews. 2005;40:65-71.
Li et al., Synthesis of Coumarin-Appended Pyridyl Tricarbonylrhenium(I) 2,2'-Bipyridyl Complexes with Oligoether Spacer and Their Fluorescence Resonance Energy Transfer Studies. Organometallics. 2009;28(6):1620-1630.
Lieu et al., The roles of iron in health and disease. Mol Aspects Med. Feb.-Apr. 2001;22(1-2):1-87.
Liu et al., Nanoparticle and iron chelators as a potential novel Alzheimer therapy. Methods Mol Biol. 2010;610:123-44. doi: 10.1007/978-1-60327-029-8_8.
Lovejoy et al., Iron chelators as anti-neoplastic agents: current developments and promise of the PIH class of chelators. Curr Med Chem. Jun. 2003;10(12):1035-49.
Luciani et al., Americium in the beagle dog: biokinetic and dosimetric model. Health Phys. May 2006;90(5):459-70.
Macpherson et al., Experimental production of diffuse colitis in rats. Digestion. 1978;17(2):135-50.
Malcovati, Impact of transfusion dependency and secondary iron overload on the survival of patients with myelodysplastic syndromes. Leuk Res. Dec. 2007;31 Suppl 3:S2-6.
Malluche et al., The Use of Deferoxamine in the Management of Aluminum Accumulation in Bone in Patients with Renal Failure. N Engl J Med. Jul. 19, 1984;311(3):140-4.
Marriott et al., Synthesis of the farnesyl ether 2,3,5-trifluoro-6-hydroxy-4-[(E,E)-3,7,11-trimethyldodeca-2,6,10-trien-l-yloxy]nitrobenzene, and related compounds containing a substituted hydroxytrifluorophenyl residue: novel inhibitors of protein farnesyltransferase, geranylgeranyltransferase I and squalene synthase. J Chem Soc Perkin Trans 1. 2000;1(24):4265-78.
Millan et al., Biological signatures of brain damage associated with high serum ferritin levels in patients with acute ischemic stroke and thrombolytic treatment. Dis Markers. 2008;25(3):181-8.
Miller et al., Efficacy of orally administered amphipathic polyaminocarboxylic acid chelators for the removal of plutonium and americium: comparison with injected Zn-DTPA in the rat. Radiat Prot Dosimetry. 2006;118(4):412-20. Epub Dec. 6, 2005.
Molina-Jijón et al., Deferoxamine pretreatment prevents Cr(VI)-induced nephrotoxicity and oxidant stress: Role of Cr(VI) chelation. Toxicol. 2012;291:93-101.

(56) References Cited

OTHER PUBLICATIONS

Naegeli et al., Metabolites of Microorganisms. Part 193. Ferrithiocin. Helv Chim Acta. 1980;63:1400-06. German.
Nash et al., Features of the thermodynamics of two-phase distribution reactions of americium(III) and europium(III) nitrates into solutions of 2,6-bis[(bis(2-ethylhexyl)phosphino)methyl]pyridine N,P,P'-trioxide. Inorg Chem. Nov. 4, 2002;41(22):5849-58.
Neu et al., Structural Characterization of a Plutonium(IV) Siderophore Complex: Single-Crystal Structure of Pu-Desferrioxamine E. Angew Chem Int Ed Engl. Apr. 2000;39(8):1442-1444.
Nisbet-Brown et al., Effectiveness and safety of ICL670 in iron-loaded patients with thalassaemia: a randomised, double-blind, placebo-controlled, dose-escalation trial. Lancet. May 10, 2003;361(9369):1597-602.
O'Connell et al., The role of iron in ferritin- and haemosiderin-mediated lipid peroxidation in liposomes. Biochem J. Jul. 1, 1985;229(1):135-9.
Olivieri et al., Iron-chelating therapy and the treatment of thalassemia. Blood. Feb. 1, 1997;89(3):739-61.
Olivieri et al., Long-term safety and effectiveness of iron-chelation therapy with deferiprone for thalassemia major. N Engl J Med. Aug. 13, 1998;339(7):417-23.
Olivieri, Long-term therapy with deferiprone. Acta Haematol. 1996;95(1):37-48.
Olivieri, Progression of iron overload in sickle cell disease. Semin Hematol. Jan. 2001;38(1 Suppl 1):57-62.
Ornelas et al., An Efficient Synthesis of Highly Functionalized Chiral Lactams. Tetrahedron Lett. 2011;52:4760-63.
Østergaard et al., Evalution of capillary electrophoresis-frontal analysis for the study of low molecular weight drug-human serum albumin interactions. Electrophoresis. Sep. 2002;23(17):2842-53.
Panter et al., Dextran-Coupled Deferoxamine Improves Outcome in a Murine Model of Head Injury. J Neurotrauma. 1992;9(1):47-53.
Paquet et al., Efficacy of 3,4,3-LI(1,2-HOPO) for decorporation of Pu, Am and U from rats injected intramuscularly with high-fired particles of MOX. Radiat Prot Dosimetry. 2003;105(1-4):521-5.
Pashalidis et al., Effective complex formation in the interaction of 1,2-dimethyl-3-hydroxypyrid-4-one (Deferiprone or L1) with uranium (VI). J Radioanal Nucl Chem. 1999;242:181-84.
Pietrangelo, Iron chelation beyond transfusion iron overload. Am J Hematol. Dec. 2007;82(12 Suppl):1142-6.
Pietrangelo, Mechanism of iron toxicity. In: Iron Chelation Therapy. Hershko, ed. 2002:19-43.
Pippard et al., Iron chelation using subcutaneous infusions of diethylene triamine penta-acetic acid (DTPA). Scand J Haematol. May 1986;36(5):466-72.
Pippard, Desferrioxamine-induced iron excretion in humans. Baillieres Clin Haematol. Apr. 1989;2(2):323-43.
Pippard, Iron overload and iron chelation therapy in thalassaemia and sickle cell haemoglobinopathies. Acta Haematol. 1987;78(2-3):206-11.
Piyamongkol et al., Novel Synthetic Approach to 2-(1'-Hydroxyalkyl)- and 2-Amido-3-Hydroxypyridin-4-ones. Tetrahderon. 2001;57:3479-86.
Ponka et al., Function and regulation of transferrin and ferritin. Semin Hematol. Jan. 1998;35(1):35-54.
Ponka et al., Mobilization of iron from reticulocytes. Identification of pyridoxal isonicotinoyl hydrazone as a new iron chelating agent. FEBS Lett. Jan. 15, 1979;97(2):317-21.
Rao et al., Complexation of Thorium(IV) with Desmethyldesferrithiocin. Radiochim Acta. 2000;88:851-56.
Raymond et al., Coordination Chemistry and Microbial Iron Transport. Acc Chem Res. 1979;12:183-190.
Re et al., Antioxidant activity applying an improved ABTS radical cation decolorization assay. Free Radic Biol Med. May 1999;26(9-10):1231-7.
Richardson, The controversial role of deferiprone in the treatment of thalassemia. J Lab Clin Med. May 2001;137(5):324-9.
Saljooghi et al., Clinical evaluation of Deferasirox for removal of cadmium ions in rat. Biometals. 2010;23:707-12.
Saljooghi, Chelation of aluminum by combining deferasirox and deferiprone in rats. Toxicol Ind Health. 2012;28(8):740-5.
Santos et al., A cyclohexane-1, 2-diyldinitrilotetraacetate tetrahydroxamate derivative for actinide complexation: Synthesis and complexation studies. J Chem Soc Dalton Trans. 2000:4398-4402.
Seligman et al., Molecular Mechanisms of Iron Metabolism. The Molecular Basis of Blood Diseases. 1987;219-44.
Shin et al., A novel trivalent cation chelator Feralex dissociates binding of aluminum and iron associated with hyperphosphorylated τ of Alzheimer's disease. Brain Res. 2003;961:139-46.
Souillac et al., "Characterization of Deliver Systems, Differential Scanning in Calorimetry." Encyclopedia of Controlled Drug Delivery. John Wiley & Sons. 1999:212-27.
Stahel et al., Iron chelators: in vitro inhibitory effect on the liver stage of rodent and human malaria. Am J Trop Med Hyg. Sep. 1988;39(3):236-40.
Stradling et al., Recent developments in the decorpoartion of plutonium, americium and thorium. Radiat Prot Dosimetry. 1998;79:445-48.
Streiff et al., Phase 1 study of N1-N11-diethylnorspermine (DENSPM) administered TID for 6 days in patients with advanced malignancies. Invest New Drugs. 2001;19(1):29-39.
Supkowski et al., Displacement of Inner-Sphere Water Molecules from Eu(3+) Analogues of Gd(3+) MRI Contrast Agents by Carbonate and Phosphate Anions: Dissociation Constants from Luminescence Data in the Rapid-Exchange Limit. Inorg Chem. Nov. 29, 1999;38(24):5616-5619.
Taetle et al., Combination iron depletion therapy. J Natl Cancer Inst. Aug. 16, 1989;81(16):1229-35.
Tang et al., High-resolution magnetic resonance imaging tracks changes in organ and tissue mass in obese and aging rats. Am J Physiol Regul Integr Comp Physiol. Mar. 2002;282(3):R890-9.
Theil et al., Ferritin Mineralization: Ferroxidation and Beyond. J Inorg Biochem. 1997;67:30. Abstract B13.
Thomas et al., Ferritin and superoxide-dependent lipid peroxidation. J Biol Chem. Mar. 25, 1985;260(6):3275-80.
Thompson et al., Protein conformational misfolding and amyloid formation: characteristics of a new class of disorders that include Alzheimer's and Prion diseases. Curr Med Chem. Oct. 2002;9(19):1751-62.
Trokowski et al., Cyclen-based phenylboronate ligands and their Eu3+ complexes for sensing glucose by MRI. Bioconjug Chem. Nov.-Dec. 2004;15(6):1431-40.
Uhlir et al., Specific sequestering agents for the actinides. 21. Synthesis and initial biological testing of octadentate mixed catecholate-hydroxypyridinonate ligands. J Med Chem. Feb. 19, 1993;36(4):504-9.
Vaidya et al., A rapid urine test for early detection of kidney injury. Kidney Int. Jul. 2009;76(1):108-14. doi: 10.1038/ki.2009.96. Epub Apr. 22, 2009.
Vaidya et al., Urinary kidney injury molecule-1: a sensitive quantitative biomarker for early detection of kidney tubular injury. Am J Physiol Renal Physiol. Feb. 2006;290(2):F517-29. Epub Sep. 20, 2005.
Vichinsky, Current issues with blood transfusions in sickle cell disease. Semin Hematol. Jan. 2001;38(1 Suppl 1):14-22.
Vippagunta et al., Crystalline solids. Adv Drug Deliv Rev. May 16, 2001;48(1):3-26.
Weintraub et al., The treatment of hemochromatosis by phlebotomy. Med Clin North Am. Nov. 1966;50(6):1579-90.
Whisenhunt et al., Specific Sequestering Agents for the Actinides. 29. Stability of the Thorium(IV) Complexes of Desferrioxamine B (DFO) and Three Octadentate Catecholate or Hydroxypyridinonate DFO Derivatives: DFOMTA, DFOCAMC, and DFO-1,2-HOPO. Comparative Stability of the Plutonium(IV) DFOMTA Complex(1). Inorg Chem. Jul. 3, 1996;35(14):4128-4136.
White et al., The effect of chelating agents on cellular iron metabolism. Clin Sci Mol Med. Mar. 1976;50(3):145-52.
White et al., The effect of chelating agents on iron mobilization in Chang cell cultures. Blood. Dec. 1976;48(6):923-9.

(56) References Cited

OTHER PUBLICATIONS

White et al., Total synthesis of geodiamolide A, a novel cyclodepsipeptide of marine origin. J Org Chem. 1989;54(4):736-738.

Wilen et al., Strategies in Optical Resolution. Tetrahedron. 1977;33:2725-36.

Woessner et al., Numerical solution of the Bloch equations provides insights into the optimum design of PARACEST agents for MRI. Magn Reson Med. Apr. 2005;53(4):790-9.

Wojcik et al., Natural history of C282Y homozygotes for hemochromatosis. Can J Gastroenterol. May 2002;16(5):297-302.

Wolfe et al., A non-human primate model for the study of oral iron chelators. Br J Haematol. Jul. 1989;72(3):456-61.

Wolff et al., A Phase II study of the polyamine analog N1,N11-diethylnorspermine (DENSpm) daily for five days every 21 days in patients with previously treated metastatic breast cancer. Clin Cancer Res. Dec. 1, 2003;9(16 Pt 1):5922-8.

Wood et al., The metabolism of iron-dextran given as a total-dose infusion to iron deficient Jamaican subjects. Br J Haematol. Feb. 1968;14(2):119-29.

Yamada et al., Role of neutrophil-derived oxidants in the pathogenesis of intestinal inflammation. Klin Wochenschr. Dec. 15, 1991;69(21-23):988-94.

Zacharski et al., Reduction of iron stores and cardiovascular outcomes in patients with peripheral arterial disease: a randomized controlled trial. JAMA. Feb. 14, 2007;297(6):603-10.

Zaman et al., Protection from oxidative stress-induced apoptosis in cortical neuronal cultures by iron chelators is associated with enhanced DNA binding of hypoxia-inducible factor-1 and ATF-1/CREB and increased expression of glycolytic enzymes, p21(waf1/cip1), and erythropoietin. J Neurosci. Nov. 15, 1999;19(22):9821-30.

Zecca et al., Neuromelanin can protect against iron-mediated oxidative damage in system modeling iron overload of brain aging and Parkinson's disease. J Neurochem. Aug. 2008;106(4):1866-75. Epub Jul. 4, 2008.

Zhang et al., A novel europium(III)-based MRI contrast agent. J Am Chem Soc. Feb. 21, 2001;123(7):1517-8.

Zhang et al., A paramagnetic CEST agent for imaging glucose by MRI. J Am Chem Soc. Dec. 17, 2003;125(50):15288-9.

Zhou et al., Comparison of kidney injury molecule-1 and other nephrotoxicity biomarkers in urine and kidney following acute exposure to gentamicin, mercury, and chromium. Toxicol Sci. Jan. 2008;101(1):159-70. Epub Oct. 13, 2007.

Zurlo et al., Survival and causes of death in thalassaemia major. Lancet. Jul. 1, 1989;2(8653):27-30.

International Search Report and Written Opinion, mailed Feb. 25, 2016, in connection with Application No. PCT/US2015/065985.

International Search Report and Written Opinion, mailed Jun. 17, 2016, in connection with Application No. PCT/US2016/024239.

Boddaert et al., Selective iron chelation in Friedreich ataxia: biologic and clinical implications. Blood. Jul. 1, 2007;110(1):401-8. Epub Mar. 22, 2007.

Cavaliere et al., The biofilm matrix destabilizers, EDTA and DNaseI, enhance the susceptibility of nontypeable Hemophilus influenzae biofilms to treatment with ampicillin and ciprofloxacin. Microbiologyopen. Aug. 2014;3(4):557-67. doi: 10.1002/mbo3.187. Epub Jul. 6, 2014.

Moreau-Marquis et al., Tobramycin and FDA-approved iron chelators eliminate Pseudomonas aeruginosa biofilms on cystic fibrosis cells. Am J Respir Cell Mol Biol. Sep. 2009;41(3):305-13. doi: 10.1165/rcmb.2008-0299OC. Epub Jan. 23, 2009.

Richardson et al., Development of potential iron chelators for the treatment of Friedreich's ataxia: ligands that mobilize mitochondrial iron. Biochim Biophys Acta. May 31, 2001;1536(2-3):133-40.

Wong et al., The Friedreich's ataxia mutation confers cellular sensitivity to oxidant stress which is rescued by chelators of iron and calcium and inhibitors of apoptosis. Hum Mol Genet. Mar. 1999;8(3):425-30.

\* cited by examiner

DESFERRITHIOCIN POLYETHER ANALOGUES

RELATED APPLICATIONS

This application is a division of and claims priority under 35 U.S.C. §120 to U.S. patent application Ser. No. 14/264,959, filed Apr. 29, 2014 and issued as U.S. Pat. No. 9,096,553, which is a continuation of and claims priority under 35 U.S.C. §120 to U.S. patent application Ser. No. 13/631,025, filed Sep. 28, 2012 and issued as U.S. Pat. No. 8,722,899, which claims priority under 35 U.S.C. §120 to and is a continuation of U.S. patent application Ser. No. 11/973,001, filed on Oct. 4, 2007 and issued as U.S. Pat. No. 8,278,458, which claims priority under 35 U.S.C. §120 to and is a continuation of International Application No. PCT/US2006/010945, which designated the United States and was filed on Mar. 22, 2006, published in English, which claims priority under 35 U.S.C. §119(e) to U.S. Provisional Application No. 60/668,045, filed on Apr. 4, 2005. The entire teachings of the above applications are incorporated herein by reference.

GOVERNMENT SUPPORT

This invention was made with government support under Grant No. DK049108 awarded by the National Institutes of Health. The government has certain rights in the invention.

BACKGROUND OF THE INVENTION

Iron metabolism in primates is characterized by a highly efficient recycling process. Consequently, there is no specific mechanism for eliminating this transition metal. Because of the lack of an iron clearance mechanism, the introduction of "excess iron" into this closed metabolic loop often leads to chronic overload and can ultimately lead to biological damage (e.g., peroxidative tissue damage). There are a number of ways in which excess iron is introduced, including a high-iron diet, acute iron ingestion or malabsorption of the metal. In each of these situations, a subject can typically be treated by phlebotomy to reduce iron levels. However, for iron-overload syndromes resulting from chronic transfusion therapy, e.g., aplastic anemia and thalassemia, phlebotomy is not an option. In these secondary iron overload syndromes, the origin of the excess iron is the transfused red blood cells. Since removing the red blood cells to remedy the iron overload would be counterproductive, an alternative method of removing iron is chelation therapy.

Although considerable effort has been invested in the development of new therapeutics for managing iron overload resulting from thalassemia, particularly therapeutics that can be administered orally, desferrioxamine B, a hexa-coordinate hydroxamate iron chelator produced by *Streptomyces pilosus*, is still the protocol of choice. However, desferrioxamine B is not ideal for chelation therapy, because iron is removed with a low efficiency. In addition, oral activity of desferrioxamine B is marginal, thereby requiring parenteral administration, which can result in poor patient compliance, particularly for patients in need of long-term chelation therapy.

A substantial number of synthetic iron chelators have been studied in recent years as potential orally active therapeutics, e.g., pyridoxal isonicotinoyl hydrazone (PIH), hydroxypyridones and N,N'-bis-(2-hydroxybenzylethylene-diamine)-N,N'-diacetic acid (HBED); however, the synthetic chelators have not yet demonstrated the desired properties (e.g., effective chelation, suitable oral activity, and acceptable toxicity). Siderophores including enterobactin and rhodotorulic acid have also been studied. However, both enterobactin and rhodotorulic acid have exhibited unacceptable toxicity and neither demonstrated measurable oral activity. In general, although a large number of siderophores and synthetic iron chelators have been developed, most have been abandoned because their properties are not suitable for use in treating chronic iron overload.

Therefore, a need still exists for novel iron chelators that can be used in chelation therapy, especially chronic chelation therapy. Suitable chelators can be efficient in chelating and removing iron from an organism, possess suitable oral bioavailability and/or pose minimal toxicity to a subject.

SUMMARY OF THE INVENTION

This application relates to compounds characterized by a structural formula selected from Structural Formulas (I), (II), and (III):

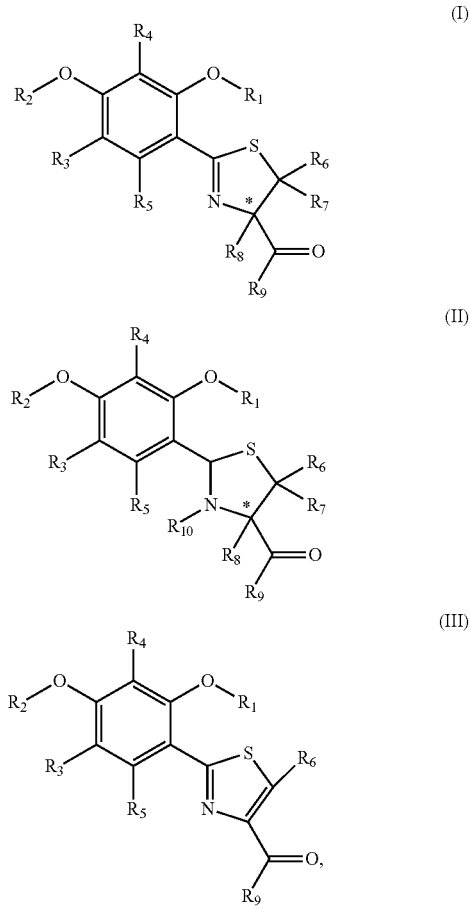

$R_1$ is —H or an acyl group;
$R_2$ is —[(CH$_2$)$_n$—O]$_x$—[(CH$_2$)$_n$—O]$_y$—R';
$R_3$, $R_4$ and $R_5$ are each independently —H, an alkyl group, or —OR$_{11}$;
$R_6$, $R_7$, and $R_8$ are each independently —H or an alkyl group;
$R_9$ is —OR$_{12}$ or —N(OH)R$_{13}$;
$R_{10}$ is —H or an alkyl group;

$R_{11}$ is —H, an alkyl group or an acyl group;
$R_{12}$ is —H or an alkyl group;
$R_{13}$ is an alkyl group,

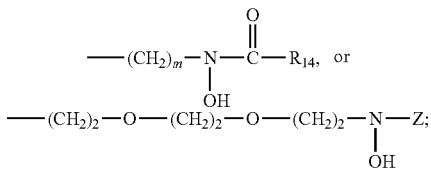

$R_{14}$ is an alkyl group;
R' is an alkyl group;
m is an integer from 1 to 8;
each n is independently an integer from 1 to 8;
x is an integer from 1 to 8;
y is an integer from 0 to 8;
Z is —C(O)$R_{14}$,

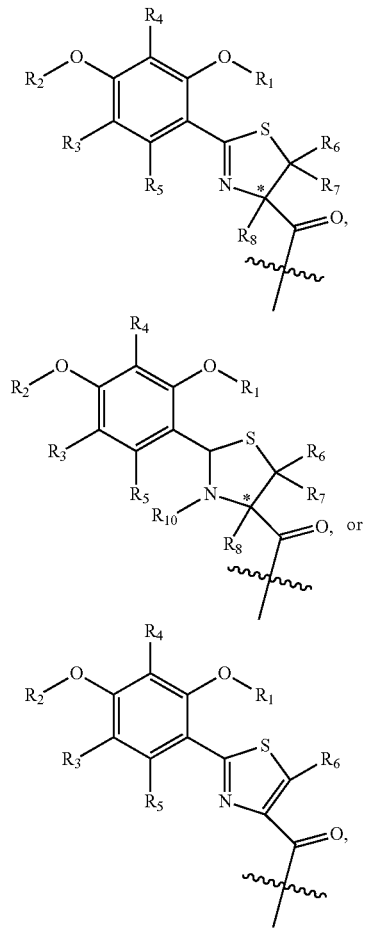

or a salt, solvate or hydrate thereof.

The invention includes pharmaceutical compositions comprising a compound of the invention in conjunction with a carrier or diluent. The pharmaceutical compositions can be for use in therapy.

In another embodiment, the present invention is a method of treating a pathological condition responsive to chelation or sequestration of a trivalent metal in a subject, comprising administering to the subject a therapeutically or prophylactically effective amount of a compound represented by a structural formula selected from Structural Formulas (I), (II), and (III) or a pharmaceutical composition including one of these compounds.

The compounds of the invention can also be used in a method of reducing oxidative stress in a subject in need of treatment therefor and a method of treating a subject who is suffering from neoplastic disease or a preneoplastic condition, in which a therapeutically effective amount of one of the compounds or pharmaceutical compositions of the invention is administered to the subject.

The invention also relates to the use of compounds disclosed herein in medical therapy. The invention further relates to the use of the compounds of the invention for the manufacture of a medicament for therapy, for example, for treating pathological conditions responsive to chelation or sequestration of metals, for reducing oxidative stress and for treating neoplastic disease or a preneoplastic condition.

The metal chelators of the invention have the advantage of having a desirable iron clearing efficiency. The metal chelators of the invention can possess a different volume of distribution from present known chelators, resulting in a different distribution among organs. This different distribution can permit penetration into organs such as the heart, brain and pancreas, as well as result in the majority of clearance of the chelators in the liver, thereby decreasing the risk of toxicity to the kidneys. Advantageously compounds of the invention exhibit a low concentration in the kidneys following administration.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
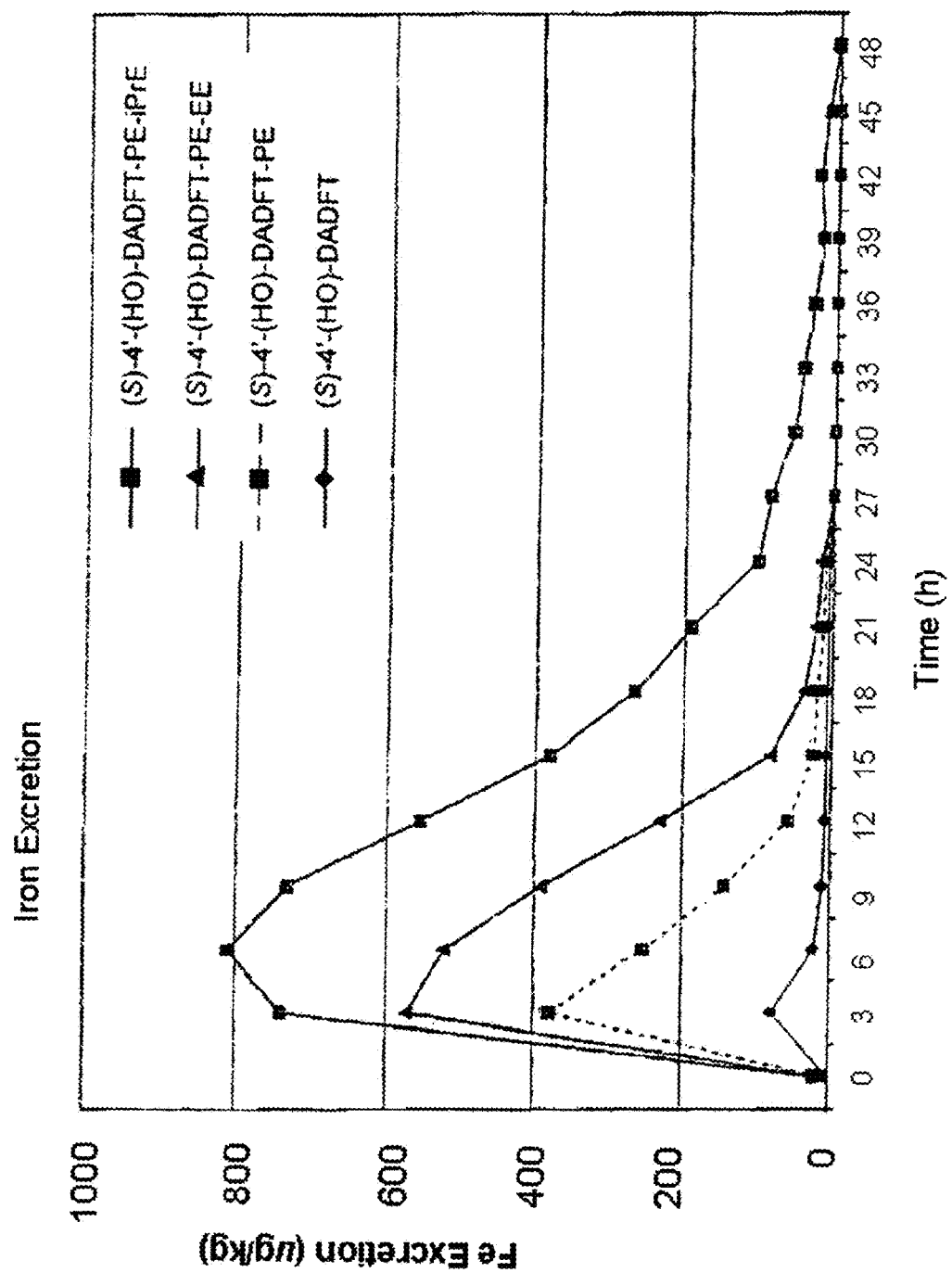
FIG. 1 shows the iron clearing efficiency of compounds of the invention in a non-iron overloaded, bile duct cannulated rat model.

Compounds of the invention are represented by a structural formula selected from Structural Formulas (I), (II), and (III) as described above.

As discussed below, stereoisomers and mixtures of stereoisomers of the compounds disclosed herein are included in the invention.

Typically, compounds of the invention are represented by Structural Formulas (I), where the variables are as defined above.

In one embodiment, $R_9$ in Structural Formulas (I)-(III) is $-OR_{12}$.

When $R_9$ is $-OR_{12}$, compounds of the invention can have one or more of the following features: (1) $R_8$ is $-H$ or $-CH_3$; (2) $R_6$ and $R_7$ are each $-H$ or $-CH_3$, preferably $-H$; (3) $R_3$, $R_4$ and $R_5$ are each $-H$; (4) $R_2$ is $-[(CH_2)_n-O]_x-R'$; n is independently 1 to 4; and x is 1 to 4; (5) $R_1$ is $-H$; and (6) R' is $-CH_3$. Preferred compounds of the invention have feature (1), more preferably features (1) and (2), and even more preferably features (1), (2) and (3). Particularly preferred compounds of the invention have features (1), (2), (3) and (4); (1), (2), (3), (4) and (5); or have all six of the above features.

Specific examples of compounds of the invention are represented by Structural Formulas (IV)-(IX):

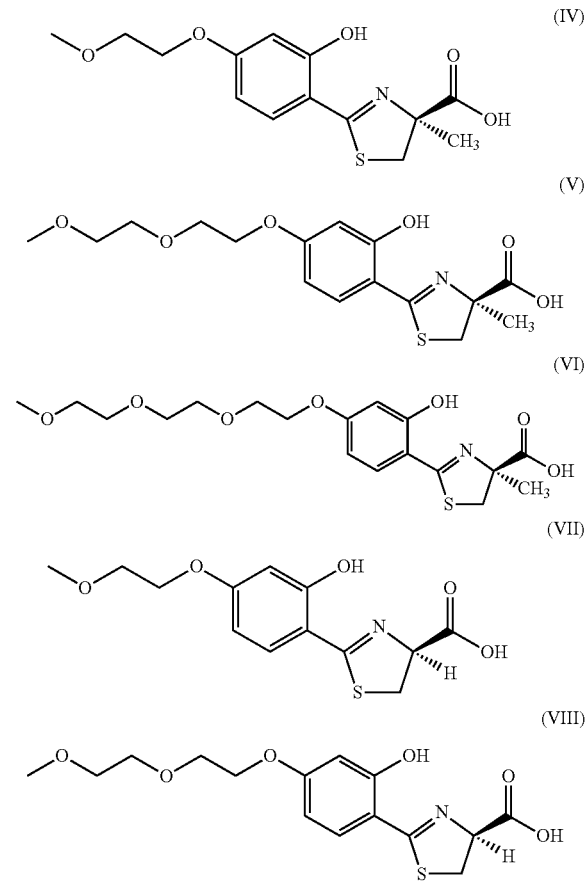

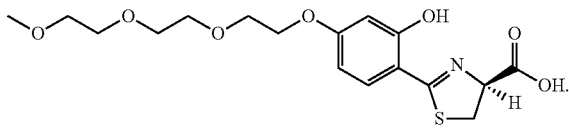

The invention also includes enantiomers and mixtures of enantiomers (e.g., racemic mixtures) of the compounds represented by Structural Formulas (I)-(IX), along with their salts (e.g., pharmaceutically acceptable salts), solvates and hydrates.

In addition to compounds represented by Structural Formulas (I)-(IX), compounds of the invention can exist in optically active forms that have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that one or more chiral carbons are non-superimposable mirror images of one another. A specific stereoisomer, which is an exact mirror image of another stereoisomer, can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). In the present application, the chiral carbon at the 4-position of the thiazoline or thiazolidine ring has been designated with an asterisk, because the configuration of this carbon is of particular interest. When bonds to chiral carbons are depicted as straight lines in the formulas of the invention, it is understood that both the (R) and (S) configurations of each chiral carbon, and hence both enantiomers and mixtures thereof, are embraced within the formula. As is used in the art, when it is desired to specify the absolute configuration about a chiral carbon, a bond to the chiral carbon can be depicted as a wedge (bonds to atoms above the plane) and another can be depicted as a series or wedge of short parallel lines (bonds to atoms below the plane). The Cahn-Ingold-Prelog system can be used to assign the (R) or (S) configuration to a chiral carbon. A chiral carbon at the 4-position of a thiazoline or thiazolidine ring preferably has an (S) configuration.

When compounds of the present invention contain one chiral center, compounds not prepared by an asymmetric synthesis exist in two enantiomeric forms and the present invention includes either or both enantiomers and mixtures of enantiomers, such as the specific 50:50 mixture referred to as a racemic mixture. The enantiomers can be resolved by methods known to those skilled in the art, for example, by formation of diastereoisomeric salts that may be separated, for example, by crystallization (See, CRC Handbook of Optical Resolutions via Diastereomeric Salt Formation by David Kozma (CRC Press, 2001)); formation of diastereoisomeric derivatives or complexes that may be separated, for example, by crystallization, gas-liquid or liquid chromatography; selective reaction of one enantiomer with an enantiomer-specific reagent, for example, enzymatic esterification; or gas-liquid or liquid chromatography in a chiral environment, for example, on a chiral support (e.g., silica with a bound chiral ligand) or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or, in other words, is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50% in an enantiomeric mixture. For example, when a mixture contains 80% of a first enantiomer and 20% of a second enantiomer, the enantiomeric excess of the first enantiomer is 60%. In the present invention, the enantiomeric excess can be about 20% or more, particularly about 40% or more, more particularly about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least about 99% enantiomeric excess. When a compound of the present invention has two or more chiral carbons (e.g., compounds of Structural Formula (II) where $R_6$ and $R_7$ are not the same), it can have more than two optical isomers and can exist in diastereomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers which are not mirror-images (e.g., (S,S) and (R,S)) are diastereomers. The diastereomeric pairs may be separated by methods known to those skilled in the art, for example, chromatography or crystallization and the individual enantiomers within each pair may be separated as described above. The present invention includes each diastereomer of such compounds and mixtures thereof.

An alkyl group is a saturated hydrocarbon in a molecule that is bonded to one other group in the molecule through a single covalent bond from one of its carbon atoms. Alkyl groups can be cyclic or acyclic, branched or unbranched (straight chained) and substituted or unsubstituted when straight chained or branched. An alkyl group typically has from 1 to about 12 carbon atoms, for example, one to about six carbon atoms or one to about four carbon atoms. Lower alkyl groups have one to four carbon atoms and include methyl, ethyl, n-propyl, iso-propyl, n-butyl, sec-butyl and tert-butyl. When cyclic, an alkyl group typically contains from about 3 to about 10 carbons, for example, from about 3 to about 8 carbon atoms, e.g., a cyclopropyl group, a cyclobutyl group, a cyclopentyl group, a cyclohexyl group, a cycloheptyl group or a cyclooctyl group.

Acyl groups are represented by the formula —C(O)R, where R is an alkyl group. Acyl groups can be hydrolyzed or cleaved from a compound by enzymes, acids, or bases. One or more of the hydrogen atoms of an acyl group can be substituted, as described below. Typically, an acyl group is removed before a compound of the present invention binds to a metal ion such as iron(III).

Suitable substituents for alkyl and acyl groups include —OH, —O(R"), —COOH, =O, —NH$_2$, —NH(R"), —N(R")$_2$, —COO(R"), —CONH$_2$, —CONH(R"), —CON(R")$_2$, and guanidine. Each R" is independently an alkyl group or an aryl group. These groups can additionally be substituted by an aryl group (e.g., an alkyl group can be substituted with an aromatic group to form an arylalkyl group). A substituted alkyl or acyl group can have more than one substituent.

Aryl groups include carbocyclic aromatic groups such as phenyl, p-tolyl, 1-naphthyl, 2-naphthyl, 1-anthracyl and 2-anthracyl. Aryl groups also include heteroaromatic groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aryl groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzoxazolyl, 2-benzimidazolyl, 1-isoquinolinyl, 3-isoquinolinyl, 1-isoindolyl and 3-isoindolyl.

Also included in the present invention are salts and pharmaceutically acceptable salts of the compounds described herein. Compounds disclosed herein that possess a sufficiently acidic functional group, a sufficiently basic functional group or both, can react with a number of organic or inorganic bases, and inorganic and organic acids, to form salts.

Acidic groups can form salts with one or more of the metals listed above, along with alkali and alkaline earth metals (e.g, sodium, potassium, magnesium, calcium). In addition, acidic groups can form salts with amines. Compounds of the invention can be supplied as a transition, lanthanide, actinide or main group metal salt. For example, the salt can be an iron (iron(II) or iron(III)) salt of a compound. As a transition, lanthanide, actinide or main group metal salt, compounds of the invention tend to form a complex with the metal. For example, if a compound of the invention is tridentate and the metal it forms a salt with has six coordinate sites, then a 2 to 1 compound to metal complex is formed. The ratio of compound to metal will vary according to the denticity of the metal and the number of coordination sites on the metal (preferably each coordination site is filled by a compound of the invention, although a coordination site can be filled with other anions such as hydroxide, halide or a carboxylate). Alternatively, the compound can be a substantially metal-free (e.g. iron-free) salt. Metal-free salts are not typically intended to encompass alkali and alkali earth metal salts. Metal-free salts are advantageously administered to a subject suffering from, for example, a metal overload condition or to an individual suffering from toxic metal exposure or from focal concentrations of metals causing untoward effects Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the hydroxide, sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

The compounds disclosed herein can be prepared in the form of their hydrates, such as hemihydrate, monohydrate, dihydrate, trihydrate, tetrahydrate and the like and as solvates.

Subjects suffering from a pathological condition responsive to chelation or sequestration of a trivalent metal can be treated with a therapeutically or prophylactically effective amount of a compound or pharmaceutical compound of the invention. One particular type of pathological condition that is responsive to chelation of a trivalent metal is a trivalent metal overload condition (e.g., an iron overload condition, an aluminum overload condition, a chromium overload condition). Another type of pathological condition that is responsive to metal chelation or sequestration is when the amount of free trivalent metal is elevated (e.g., in the serum or in a cell), such as when there is insufficient storage capacity for trivalent metals or an abnormality in the metal storage system that leads to metal release.

Iron overload conditions or diseases can be characterized by global iron overload or focal iron overload. Global iron overload conditions generally involve an excess of iron in multiple tissues or excess iron located throughout an organism. Global iron overload conditions can result from excess uptake of iron by a subject, excess storage and/or retention of iron, from, for example, dietary iron or blood transfusions. One global iron overload condition is primary hemochromatosis, which is typically a genetic disorder. A second global iron overload condition is secondary hemochromatosis, which is typically the result of receiving multiple (chronic) blood transfusions. Blood transfusions are often required for subjects suffering from thalassemia or sickle cell anemia. A type of dietary iron overload is referred to as Bantu siderosis, which is associated with the ingestion of home-brewed beer with high iron content.

In focal iron overload conditions, the excess iron is limited to one or a few cell types or tissues or a particular organ. Alternatively, symptoms associated with the excess iron are limited to a discrete organ, such as the heart, lungs, liver, pancreas, kidneys or brain. It is believed that focal iron overload can lead to neurological or neurodegenerative disorders such as Parkinson's disease, Alzheimer's disease, Huntington's disease, neuroferritinopathy, amyotrophic lateral sclerosis and multiple sclerosis.

Pathological conditions that benefit from metal chelation or sequestration are often associated with deposition of the metal in the tissues of a subject. Deposition can occur globally or focally, as described above.

A subject in need of oxidative stress reduction can have one or more of the following conditions: decreased levels of reducing agents, increased levels of reactive oxygen species, mutations in or decreased levels of antioxidant enzymes (e.g., Cu/Zn superoxide dismutase, Mn superoxide dismutase, glutathione reductase, glutathione peroxidase, thioredoxin, thioredoxin peroxidase, DT-diaphorase), mutations in or decreased levels of metal-binding proteins (e.g., transferrin, ferritin, ceruloplasmin, albumin, metallothionein), mutated or overactive enzymes capable of producing superoxide (e.g., nitric oxide synthase, NADPH oxidases, xanthine oxidase, NADH oxidase, aldehyde oxidase, dihydroorotate dehydrogenase, cytochrome c oxidase), and radiation injury. Increased or decreased levels of reducing agents, reactive oxygen species, and proteins are determined relative to the amount of such substances typically found in healthy persons.

A subject in need of oxidation stress reduction can be suffering from an ischemic episode. Ischemic episodes can occur when there is mechanical obstruction of the blood supply, such as from arterial narrowing or disruption. Myocardial ischemia, which can give rise to angina pectoris and myocardial infarctions, results from inadequate circulation of blood to the myocardium, usually due to coronary artery disease. Ischemic episodes in the brain that resolve within 24 hours are referred to as transient ischemic attacks. A longer-lasting ischemic episode, a stroke, involves irreversible brain damage, where the type and severity of symptoms depend on the location and extent of brain tissue whose access to blood circulation has been compromised. A subject at risk of suffering from an ischemic episode typically suffers from atherosclerosis, other disorders of the blood vessels, increased tendency of blood to clot, or heart disease. The compounds of this invention can be used to treat these disorders.

A subject in need of oxidation stress reduction can be suffering from inflammation. Inflammation is a fundamental pathologic process consisting of a complex of cytologic and chemical reactions that occur in blood vessels and adjacent tissues in response to an injury or abnormal stimulation caused by a physical, chemical, or biologic agent. Inflammatory disorders are characterized inflammation that lasts for an extended period (i.e., chronic inflammation) or that damages tissue. Such inflammatory disorders can affect a wide variety of tissues, such as respiratory tract, joints, bowels, and soft tissue. The compounds of this invention can be used to treat these disorders.

Although not bound by theory, it is believed that the compounds of the invention derive their ability to reduce oxidative stress through various mechanisms. In one mechanism, the compound binds to a metal, particularly a redox-active metal (e.g., iron), and fills all of the coordination sites of the metal. When all of the metal coordination sites are filled, it is believed that oxidation and/or reducing agents have a diminished ability to interact with the metal and cause redox cycling. In another mechanism, the compound stabilizes the metal in a particular oxidation state, such that it is less likely to undergo redox cycling. In yet another mechanism, the compound itself has antioxidant activity (e.g., free radical scavenging, scavenging of reactive oxygen or nitrogen species). Desferrithiocin and its derivatives and analogues are known to have intrinsic antioxidant activity, as described in U.S. Application Publication No. 2004/0044220, published Mar. 4, 2004, and U.S. Application Publication No. 2004/0132789, published Jul. 8, 2004 and PCT Application No. WO2004/017959, published Mar. 4, 2004, US Application Publication No. 2003/0236417, published Dec. 25, 2003, and U.S. Pat. Nos. 6,083,966, 6,559, 315, 6,525,080, 6,521,652 the contents of each of which are incorporated herein by reference.

Imaging or examining one or more organs, tissues, tumors or a combination thereof can be conducted after a metal salt of a compound of the invention is administered to a subject. The methods of imaging and examining are intended to encompass various instrumental techniques used for diagnosis, such as x-ray methods (including CT scans and conventional x-ray images), magnetic imaging (magnetic resonance imaging, electron paramagnetic resonance imaging) and radiochemical methods. Typically, the metal salts used in imaging or examining serve as a contrast agent. Therefore in one embodiment the metal complexes or metal salts of compounds of the present invention can be used as contrast agents for example in imaging or examining one or more organs, for example, the gastrointestinal tract.

Metals that can serve as contrast agents include gadolinium, iron, manganese, chromium, dysprosium, technetium, scandium, barium, aluminum and holmium, preferably as trications. Radioactive metal salts can be made from isotopes including $^{241}$Am, $^{51}$Cr, $^{60}$Co, $^{57}$Co, $^{58}$Co, $^{64}$Cu, $^{153}$Gd, $^{67}$Ga, $^{198}$Au, $^{113m}$In, $^{111}$In, $^{59}$Fe, $^{55}$Fe, $^{197}$Hg, $^{203}$Hg, $^{99m}$Tc, $^{201}$Tl and $^{169}$Yb, again preferably when the metal is present as a trication.

Neoplastic disease is characterized by an abnormal tissue that grows by cellular proliferation more rapidly than normal tissue. The abnormal tissue continues to grow after the stimuli that initiated the new growth cease. Neoplasms show a partial or complete lack of structural organization and functional coordination with the normal tissue, and usually form a distinct mass of tissue that may be either benign or malignant. Neoplasms can occur, for example, in a wide variety of tissues including brain, skin, mouth, nose, esophagus, lungs, stomach, pancreas, liver, bladder, ovary, uterus, testicles, colon, and bone, as well as the immune system (lymph nodes) and endocrine system (thyroid gland, parathyroid glands, adrenal gland, thymus, pituitary gland, pineal gland). The compounds of this invention can be used to treat these disorders.

Examples of tumors or cancers that can be treated by the invention include, but are not limited to, leukemia, Hodgkin's disease, non-Hodgkin's lymphomas, multiple myeloma, macroglobulinemia, polycythemia vera, lung tumors, head and neck tumors, brain tumors (neuroblastoma), endometrial tumors, ovarian tumors, cervical tumors, breast tumors, choriocarcinoma, testical tumors, prostate tumor, Wilms' tumor, thyroid tumors, adrenal tumors, stomach tumor, pancreal tumors, colonic tumors, carcinoids, insulinoma, bone tumors (osteogenic sarcoma), miscellaneous sarcomas and skin cancer (melanoma).

A preneoplastic condition precedes the formation of a benign or malignant neoplasm. A precancerous lesion typically forms before a malignant neoplasm. Preneoplasms include photodermatitis, x-ray dermatitis, tar dermatitis, arsenic dermatitis, lupus dermatitis, senile keratosis, Paget disease, condylomata, burn scar, syphilitic scar, fistula scar, ulcus cruris scar, chronic ulcer, varicose ulcer, bone fistula, rectal fistula, Barrett esophagus, gastric ulcer, gastritis, cholelithiasis, kraurosis vulvae, nevus pigmentosus, Bowen dermatosis, xeroderma pigmentosum, erythroplasia, leukoplakia, Paget disease of bone, exostoses, ecchondroma, osteitis fibrosa, leontiasis ossea, neurofibromatosis, polyposis, hydatidiform mole, adenomatous hyperplasia, and struma nodosa. The compounds of this invention can be used to treat these disorders.

A "subject" is typically a human, but can also be an animal in need of treatment, e.g., companion animals (e.g., dogs, cats, and the like), farm animals (e.g., cows, pigs, horses, sheep, goats and the like) and laboratory animals (e.g., rats, mice, guinea pigs, non-human primates and the like).

The compounds and pharmaceutical compositions of the present invention can be administered by an appropriate route. Suitable routes of administration include, but are not limited to, orally, intraperitoneally, subcutaneously, intramuscularly, transdermally, rectally, sublingually, intravenously, buccally or via inhalation. Preferably, compounds and pharmaceutical compositions of the invention are administered orally.

The pharmaceutical compositions of the invention preferably contain a pharmaceutically acceptable carrier or diluent suitable for rendering the compound or mixture administrable orally, parenterally, intravenously, intradermally, intramuscularly or subcutaneously, rectally, via inhalation or via buccal administration, or transdermally. The active ingredients may be admixed or compounded with a conventional, pharmaceutically acceptable carrier or diluent. It will be understood by those skilled in the art that a mode of administration, vehicle or carrier conventionally employed and which is inert with respect to the active agent may be utilized for preparing and administering the pharmaceutical compositions of the present invention. Illustrative of such methods, vehicles and carriers are those described, for example, in Remington's Pharmaceutical Sciences, 18th ed. (1990), the disclosure of which is incorporated herein by reference.

The formulations of the present invention for use in a subject comprise the agent, together with one or more acceptable carriers or diluents therefor and optionally other therapeutic ingredients. The carriers or diluents must be "acceptable" in the sense of being compatible with the other ingredients of the formulation and not deleterious to the recipient thereof. The formulations can conveniently be presented in unit dosage form and can be prepared by any of the methods well known in the art of pharmacy. All methods include the step of bringing into association the agent with the carrier or diluent which constitutes one or more accessory ingredients. In general, the formulations are prepared by uniformly and intimately bringing into association the agent with the carriers and then, if necessary, dividing the product into unit dosages thereof.

Forms suitable for oral administration include tablets, troches, capsules, elixirs, suspensions, syrups, wafers, chewing gum or the like prepared by art recognized procedures. The amount of active compound in such therapeutically useful compositions or preparations is such that a suitable dosage will be obtained.

A syrup formulation will generally consist of a suspension or solution of the compound or salt in a liquid carrier, for example, ethanol, glycerine or water, with a flavoring or coloring agent. Where the composition is in the form of a tablet, one or more pharmaceutical carriers routinely used for preparing solid formulations can be employed. Examples of such carriers include magnesium stearate, starch, lactose and sucrose. Where the composition is in the form of a capsule, the use of routine encapsulation is generally suitable, for example, using the aforementioned carriers in a hard gelatin capsule shell. Where the composition is in the form of a soft gelatin shell capsule, pharmaceutical carriers routinely used for preparing dispersions or suspensions can be considered, for example, aqueous gums, celluloses, silicates or oils, and are incorporated in a soft gelatin capsule shell.

Formulations suitable for parenteral administration conveniently include sterile aqueous preparations of the agents that are preferably isotonic with the blood of the recipient. Suitable carrier solutions include phosphate buffered saline, saline, water, lactated ringers or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization.

Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

A typical suppository formulation includes the compound or a pharmaceutically acceptable salt thereof which is active when administered in this way, with a binding and/or lubricating agent, for example, polymeric glycols, gelatins, cocoa-butter or other low melting vegetable waxes or fats.

Typical transdermal formulations include a conventional aqueous or non-aqueous vehicle, for example, a cream, ointment, lotion or paste or are in the form of a medicated plastic, patch or membrane.

Typical compositions for inhalation are in the form of a solution, suspension or emulsion that can be administered in the form of an aerosol using a conventional propellant such as dichlorodifluoromethane or trichlorofluoromethane.

The therapeutically effective amount of a compound or pharmaceutical composition of the invention depends, in each case, upon several factors, e.g., the health, age, gender, size and condition of the subject to be treated, the intended mode of administration, and the capacity of the subject to incorporate the intended dosage form, among others. A therapeutically effective amount of an active agent is an amount sufficient to have the desired effect for the condition being treated. For example, in a method of treating of a neoplastic or a preneoplastic condition, the desired effect is partial or total inhibition, delay or prevention of the progression of cancer or the tumor including cancer metastasis; inhibition, delay or prevention of the recurrence of cancer or the tumor including cancer metastasis; or the prevention of the onset or development of cancer or a tumor (chemoprevention) in a mammal, for example a human. In a method of treating a subject with a condition treatable by chelating or sequestering a metal ion, a therapeutically effective amount of an active agent is, for example, an amount sufficient to reduce the burden of the metal in the subject, reduce the symptoms associated with the metal ion or prevent, inhibit or delay the onset and/or severity of symptoms associated with the presence of the metal. In a method of reducing oxidative stress in a subject in need of treatment thereof, a therapeutically effective amount of an active agent is, for example, an amount sufficient to reduce symptoms associated with oxidative stress or prevent, inhibit or delay the onset and/or severity of symptoms associated with oxidative stress.

A typical total daily dose of a compound of the invention to be administered to a subject (assuming an average 70 kg subject) is from approximately 5 mg to approximately 10,000 mg, (for example 0.07 mg/kg to 143 mg/kg) and preferably from approximately 50 mg to approximately 5,000 mg approximately 100 mg to approximately 2,000 mg approximately 300 mg to approximately 1,000 mg. For iron overload therapy, a daily dose of a compound of the invention should remove a minimum of from approximately 0.25 to approximately 0.40 mg of iron per kilogram of body mass per day. The dosage can be administered orally in several, for example, one, two, three, four, six, eight, twelve, or more, individual doses.

The present invention will now be illustrated by the following Examples, which are not intended to be limiting in any way.

EXEMPLIFICATION

Scheme 1. (S)-4,5-dihydro-2-[2-hydroxy-4-[2-[2-(2-methoxyethoxy)ethoxy]ethoxy]phenyl]-4-methyl-4-thiazolecarboxylic acid (1) and Ethyl Ester (2)

Reagents: (a) 50% molar excess NaOEtH, EtOH, 33%; (b) 50% NaOH, CH$_3$OH, 91%.

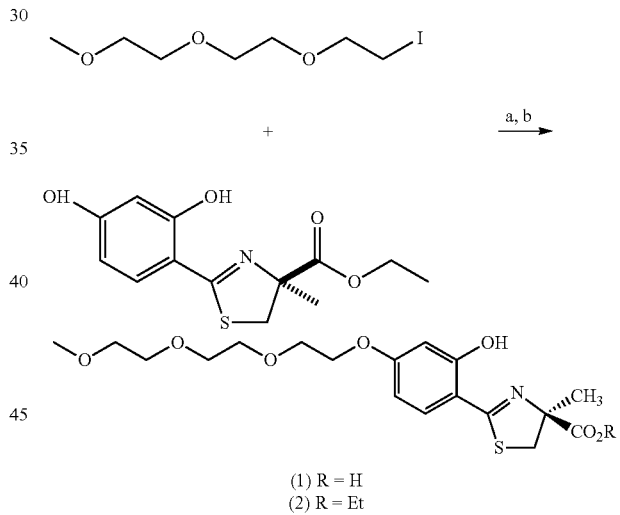

(1) R = H
(2) R = Et

Example 1

Synthesis of (S)-4,5-Dihydro-2-[2-hydroxy-4-[2-[2-(2-methoxyethoxyl)ethoxy]ethoxy]phenyl]-4-methyl-4-thiazolecarboxylic Acid (1) and Ethyl Ester (2)

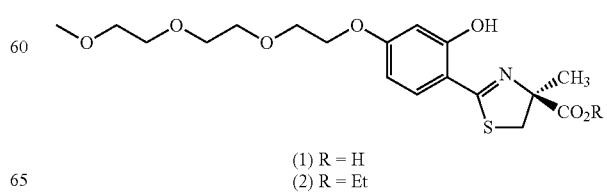

(1) R = H
(2) R = Et

The ethyl ester of (S)-2-(2,4-dihydroxyphenyl)-4,5-dihydro-4-methyl-4-thiazolecarboxylic acid ((S)-4'-(HO)-DADFT) was treated with a 50% excess of NaOEt and heated with 3,6,9-trioxa-1-iododecane (1.3 equiv) in EtOH which effected regiospecific alkylation at the 4' hydroxyl, resulting in adduct (2) (Scheme 1). Saponification of ester (2) with NaOH in aqueous methanol at room temperature gave (S)-DADFT analogue (1) (referred to herein as (S)-4'-(OH)-DADFT-PE). $^1$H NMR: ($D_2O$) δ 1.76 (s, 3H), 3.35 (s, 3H), 3.54-3.61 (m, 3H), 3.64-3.72 (m, 4H), 3.74-3.78 (m, 2H), 3.90-3.94 (m, 2H), 3.96 (d, 1H, J=12.0), 4.25-4.29 (m, 2H), 6.53 (d, 1H J=2.4), 6.4 (dd, 1H, J=9.0, 2.2), 7.61 (d, 1H, J=9.2).

Example 2

Iron Clearing Efficiency of Iron Chelators in a Non-Iron Overloaded, Bile Duct Cannulated Rat Model Studies were performed in the non-iron overloaded, bile duct cannulated rodent model with the compounds shown below.

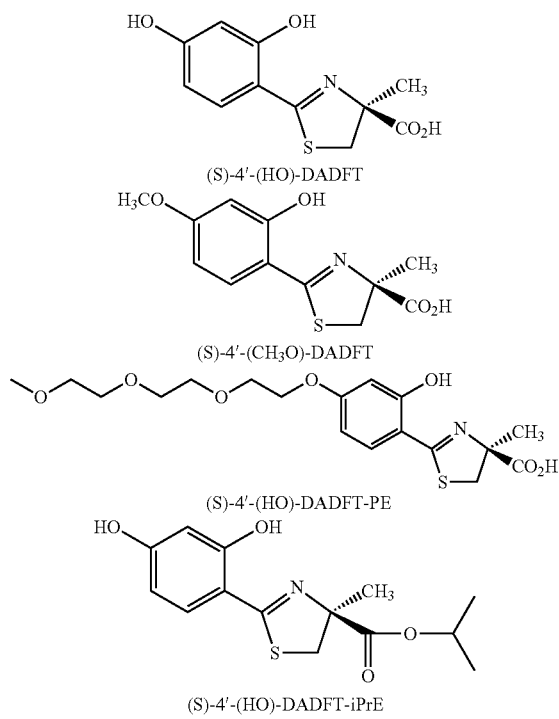

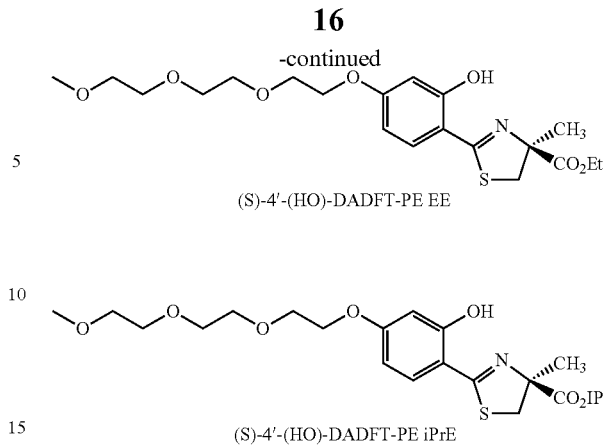

Briefly, male Sprague-Dawley rats averaging 450 g were housed in Nalgene plastic metabolic cages during the experimental period and given free access to water. The animals were anesthetized using sodium pentobarbital (55 mg/kg) administered intraperitoneally. The bile duct was cannulated using 22-gauge polyethylene tubing. The cannula was inserted into the duct about 1 cm from the duodenum and tied snugly in place. After threading through the shoulder, the cannula was passed from the rat to the swivel inside a metal torque-transmitting tether, which was attached to a rodent jacket around the animal's chest. The cannula was directed from the rat to a Gilson microfraction collector (Middleton, Wis.) by a fluid swivel mounted above the metabolic cage. Three hour bile samples were continuously collected for a minimum of 24 hours up to 48 hours. However, the efficiency calculations are based on the 24 hour iron excretion. The efficiency of each chelator was calculated on the basis of a 2:1 ligand-iron complex. The efficiencies in the rodent model were calculated by subtracting the iron excretion of control animals from the iron excretion of treated animals. This number was then divided by the theoretical output; the result is expressed as a percentage (Bergeron, R. J., et al., *J. Med Chem.* 42:95-108 (1999) the entire contents of which are incorporated herein by reference). The urine sample was taken at 24 hours and handled as previously described in Bergeron, R. J., et al., *J. Med. Chem.* 34:2072-2078 (1991), the entire contents of which are incorporated herein by reference.

The results of the evaluations are presented in Table 1 and FIG. 1.

TABLE 1

Iron Clearing Efficiencies of Compounds Tested in the Bile Duct Cannulated Rat

| Compound | Dose (mg/kg) | (μmol/kg) | Route | Vehicle | N | Efficiency (%) |
|---|---|---|---|---|---|---|
| (S)-4'-(HO)-DADFT | 76 | 300 | p.o.+ | $dH_2O$* | 3 | 1.0 ± 0.4 |
| (S)-4'-(HO)-DADFT | 76 | 300 | s.c.+ | $dH_2O$* | 4 | 1.1 ± 0.6 |
| (S)-4'-(HO)-DADFT-PE | 120 | 300 | p.o. | $dH_2O$ | 5 | 6.6 ± 1.9 |
| (S)-4'-(HO)-DADFT-PE | 120 | 300 | s.c. | $dH_2O$ | 4 | 8.7 ± 2.8 |
| (S)-4'-(HO)-DADFT-PE EE | 128 | 300 | s.c. | 50% EtOH | 3 | 11.4 ± 0.8 |
| (S)-4'-(HO)-DADFT-PE iPrE | 133 | 300 | s.c. | 50% EtOH | 3 | 25.9 ± 9.2 |
| (S)-4'-(HO)-DADFT-PE iPrE | 133 | 300 | p.o. | 40% cremophor | 3 | 9.2 ± 4.4 |

TABLE 1-continued

Iron Clearing Efficiencies of Compounds Tested in the Bile Duct Cannulated Rat

| Compound | Dose (mg/kg) | (μmol/kg) | Route | Vehicle | N | Efficiency (%) |
|---|---|---|---|---|---|---|
| (S)-4'-(HO)-DADFT-iPrE | 88 | 300 | s.c. | 50% EtOH/dH$_2$O | 3 | 1.98 ± 0.91 |
| (S)-4'-(CH$_3$O)-DADFT | 80 | 300 | p.o. | 40% Cremophor | 4 | 6.6 ± 2.8 |

†p.o. is by mouth, s.c is subcutaneously
*brought to neutral pH with NaOH solution A comparison of the iron clearing efficiency of the polyethers (S)-4-(OH)-DADFT-PE, (S)-4-(HO)-DADFT-PE EE and (S)-4-(HO)-DADFT-PE iPrE, with that of the parent drug (S)-4-(HO)-DADFT clearly shows the polyethers and their corresponding esters to work better than the parent drug. The most notable feature regarding the esters is the performance of the isopropylester iPrE vs the ethyl ester EE when both are administered subcutaneously. The iPrE is significantly more efficient. It is important to note that all drugs are administered at the same micromole per kilogram dose.

Example 3

Iron Chelators in a *Cebus apella* Monkey Model

Studies were performed in the iron-overloaded monkey model with the compounds shown below:

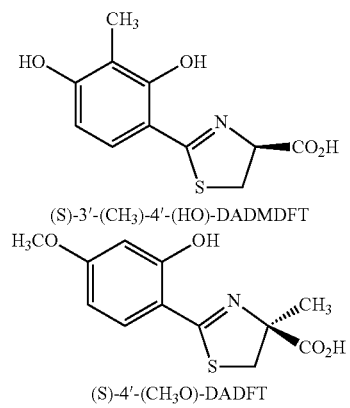

(S)-3'-(CH$_3$)-4'-(HO)-DADMDFT (S)-4'-(CH$_3$O)-DADFT

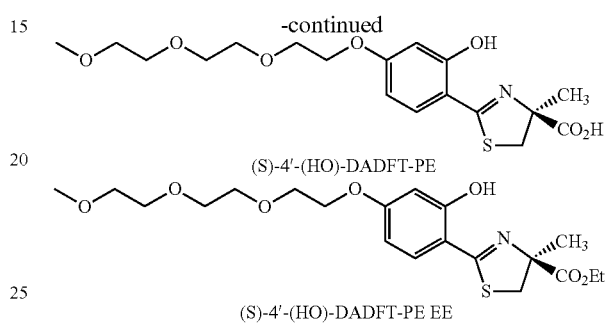

(S)-4'-(HO)-DADFT-PE (S)-4'-(HO)-DADFT-PE EE

The protocol used can be found in Bergeron, R. J. et al., "Methoxylation of Desazadesferrithiocin Analogues: Enhanced Iron Clearing Efficiency," *J. Med. Chem.* 46:1470-1477 (2003), the contents of which are incorporated herein by reference. Briefly, the monkeys were iron overloaded with iron dextran administered intravenously to result in an iron loading of about 500 mg per kg of body weight. At least 20 half-lives, 60 days, elapsed before the animals were used in experiments evaluating iron chelators. The iron chelators were suspended in vehicle and administered either p.o. or s.c. as indicated in Table 2. Fecal and urine samples were collected at 24 hour intervals beginning 4 days prior to the administration of an iron chelator and continued for 5 days after the chelator was administered. Iron concentrations in stool and urine were determined by flame atomic absorption spectroscometry. Iron chelator efficiency was calculated by dividing the net iron clearance [total iron excretion (stool plus urine) minus background] by the theoretical iron clearance and multiplying by 100. The theoretical clearance of the iron chelator was generated on the basis of a 2:1 ligand/iron complex.

The results of the evaluations are presented in Table 2.

TABLE 2

Iron Clearing Efficiencies of Compounds Tested in *Cebus apella* primates

| Compound | Dose (mg/kg) | Route | Vehicle | N | Efficiency (%) |
|---|---|---|---|---|---|
| (S)-3'-(HO)-DADMDFT | 39.1 | p.o. | buffer | 1 | 0.8 |
| (S)-5'-(HO$_2$C)-DADMDFT | 40.1 | p.o. | buffer | 1 | 0.7 |
| (S)-3'-(CH$_3$)-4'-(HO)-DADMDFT | 38.0 | p.o. | buffer | 1 | 4.0 |
| (S)-4'-(HO)-DADFT | 38 | p.o. | buffer | 4 | 14 ± 3.3 |
| (S)-4'-(HO)-DADFT | 38 | s.c. | water | 4 | 16.6 ± 2.7 |
| (S)-4'-(CH$_3$O)-DADFT | 40.1 | s.c. | buffer | 4 | 33.7 ± 12.1 |
| (S)-4'-(HO)-DADFT-PE | 59.9 | p.o. | dH$_2$O | 4 | 25.4 ± 7.4 |
| (S)-4'-(HO)-DADFT-PE | 59.9 | s.c. | dH$_2$O | 4 | 30.4 ± 7.2 |
| (S)-4'-(HO)-DADFT-PE-EE | 64.1 | s.c. | 50% EtOH/dH$_2$O | 2 | 17.9 ± 1.0 |

The data shows that the (S)-4'-(HO)-DADFT-PE given either p.o. or s.c. is at least as efficient as (S)-4'-(HO)-DADFT at clearing iron when given to primates.

Example 4

Tissue Distribution of a Polyether-Substituted (S)-4'-Hydroxydesazadesferrithiocin Analogue [(S)-4'-(HO)-DADFT-PE] upon Subcutaneous Administration to Rats

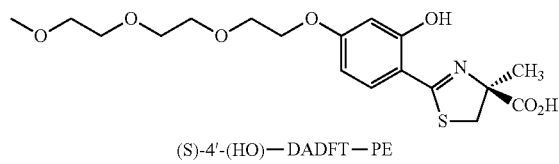

(S)-4'-(HO)—DADFT—PE

A measurement was made assessing (S)-4'-(HO)-DADFT-PE and (S)-4'-(HO)-DADFT tissue and plasma concentrations upon subcutaneous administration at times from 2-8 h post dosing. The rats were given this compound subcutaneously at 300 μmol/kg. The tissue and plasma level were obtained as described in Bergeron et al. *J. Med Chem.* 48:821-831 (2005), the entire contents of which are incorporated herein by reference. The results are shown in Table 3 and FIG. 2-FIG. 8.

Figure 2:
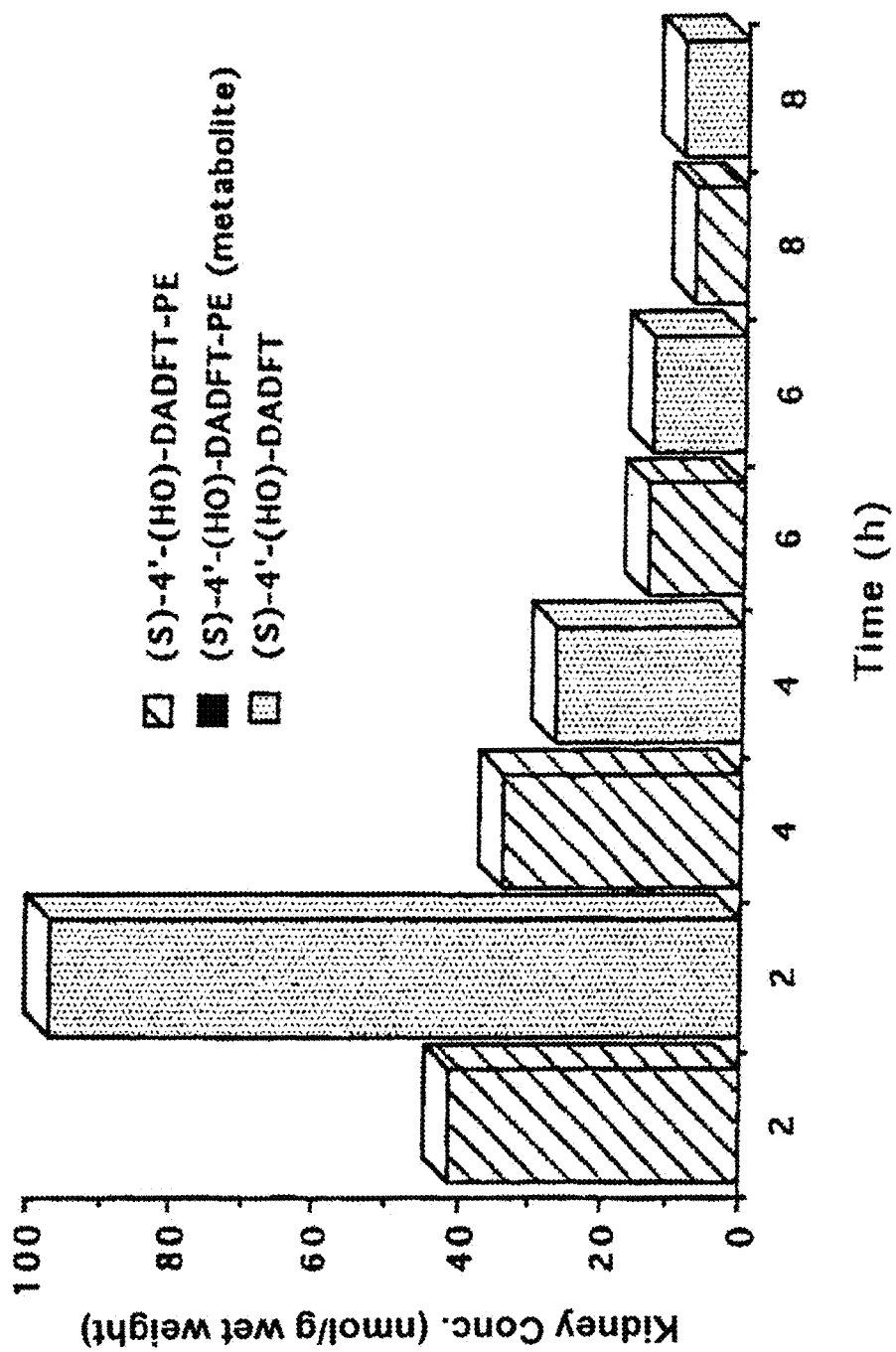
FIG. 2 shows the distribution of compounds of the invention in the kidneys of rodents over time following subcutaneous administration.
Figure 3:
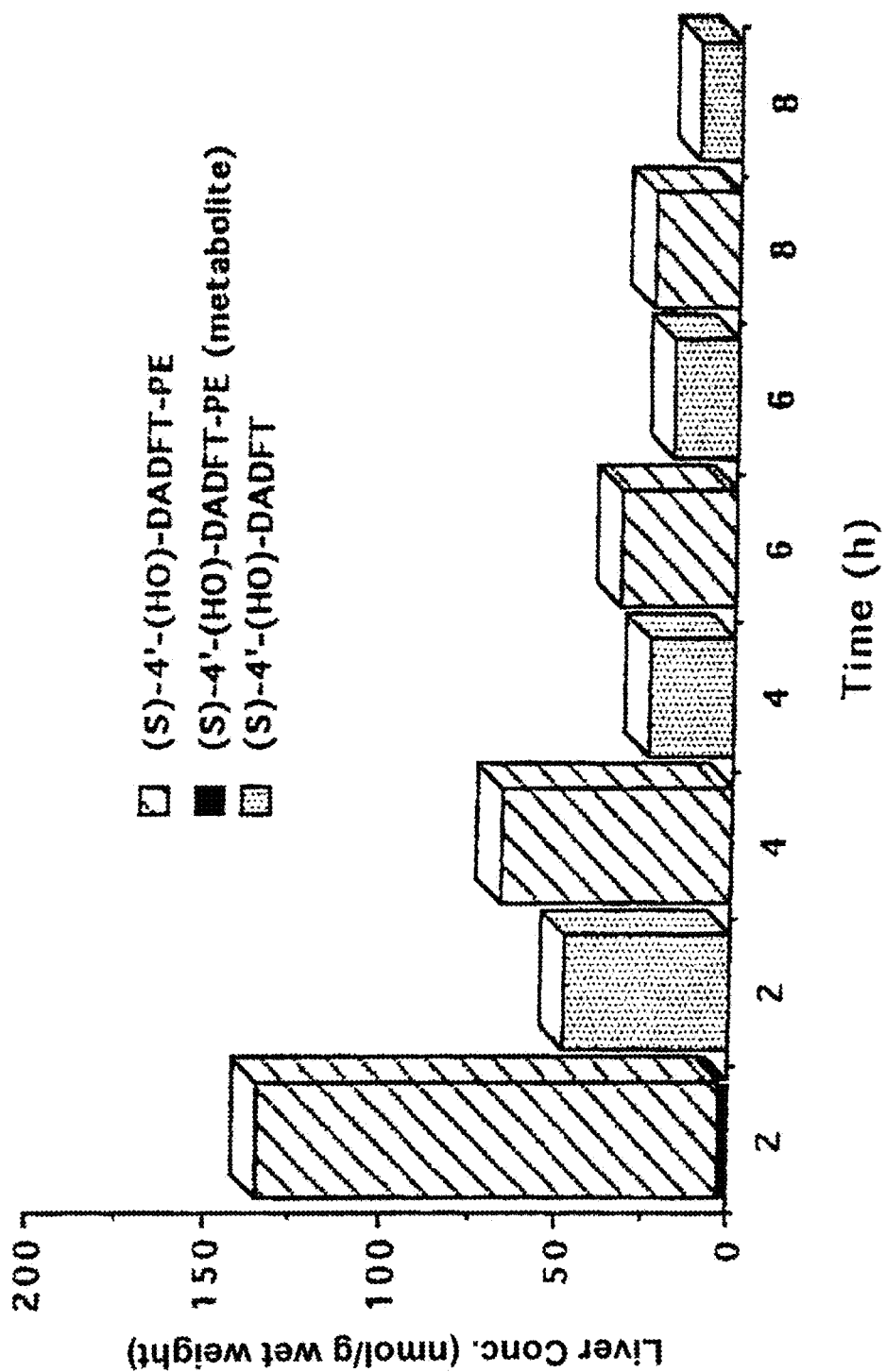
FIG. 3 shows the distribution of compounds of the invention in the liver of rodents over time following subcutaneous administration.
Figure 4:
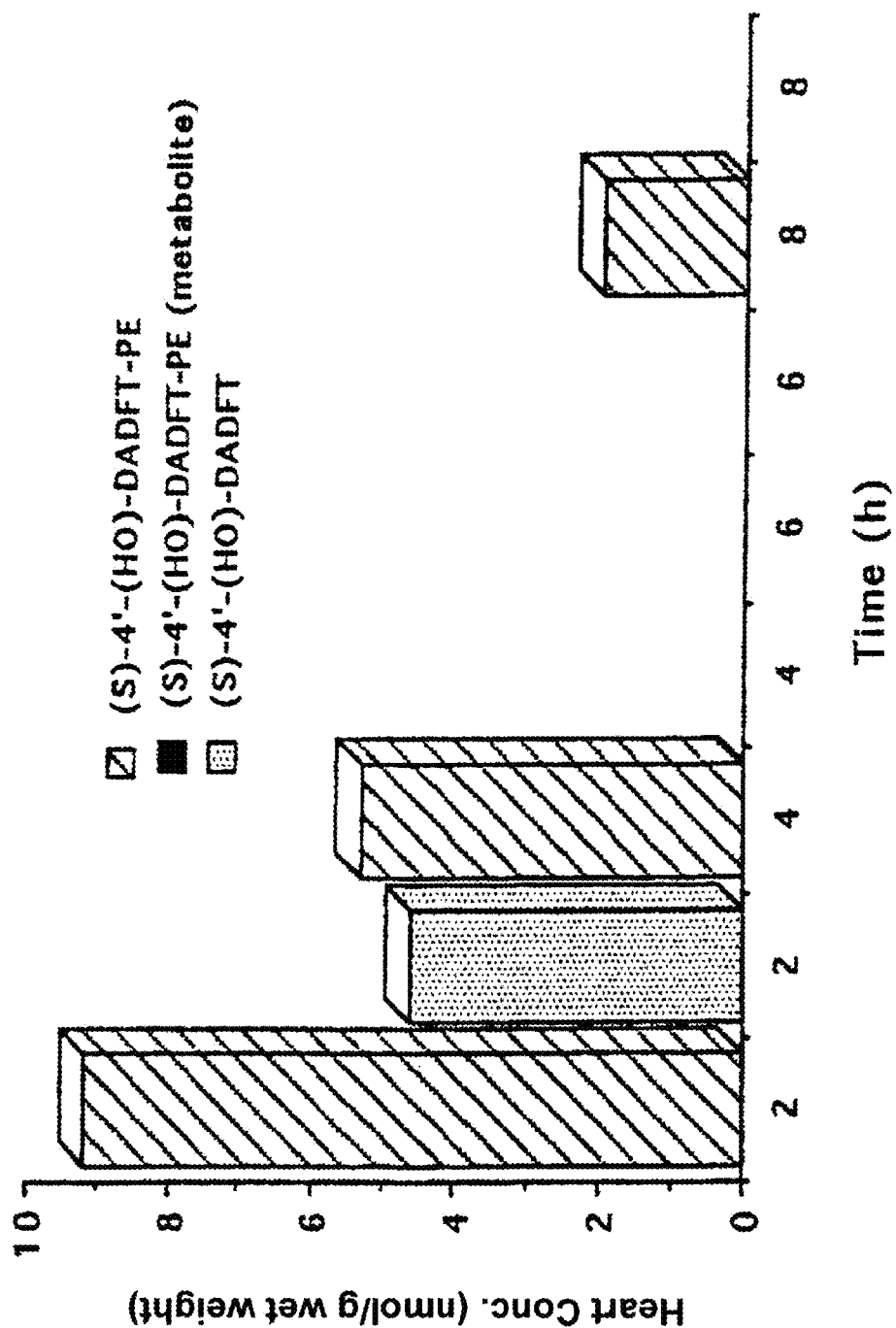
FIG. 4 shows the distribution of compounds of the invention in the heart of rodents over time following subcutaneous administration.
Figure 5:
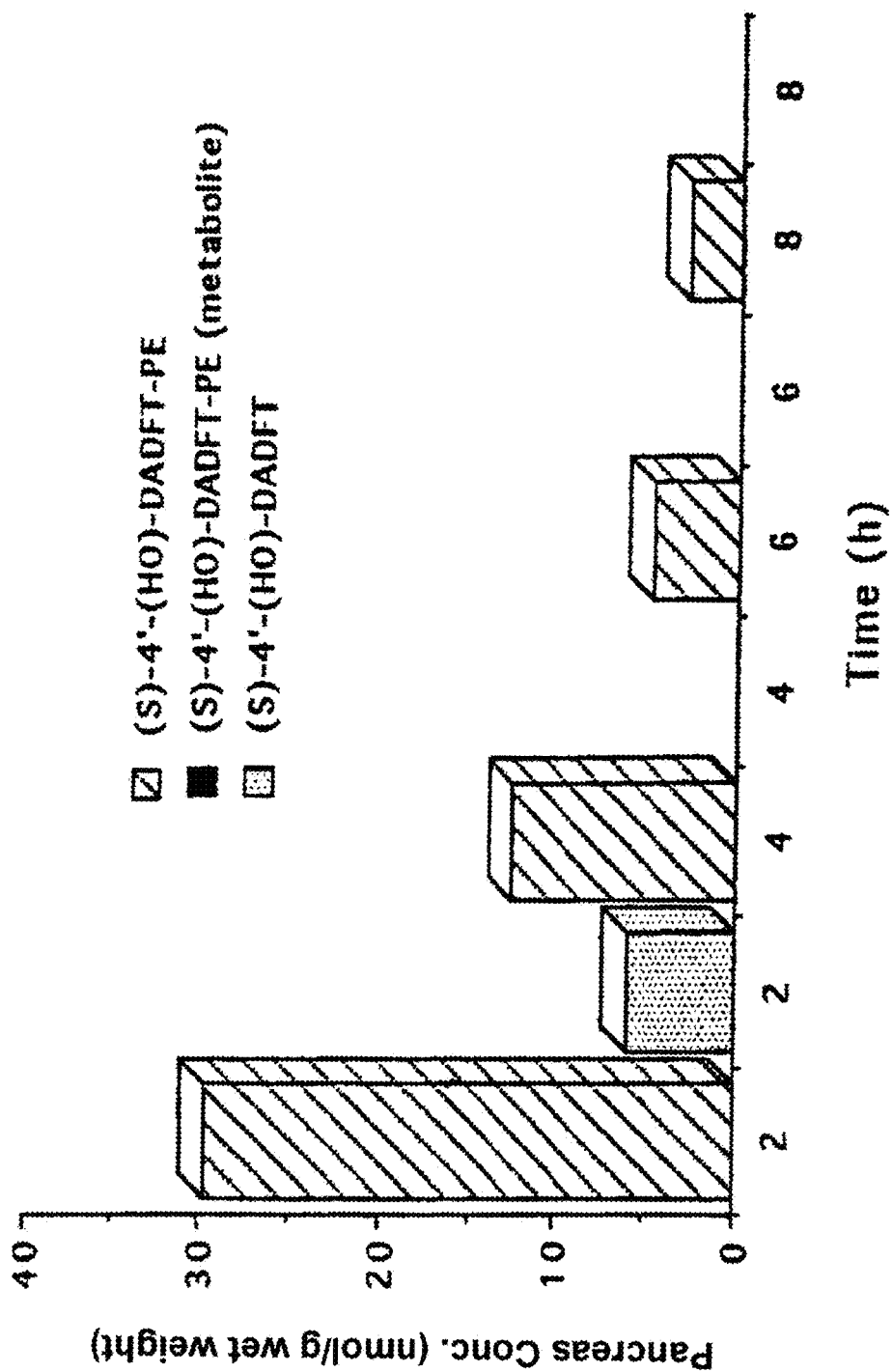
FIG. 5 shows the distribution of compounds of the invention in the pancreas of rodents over time following subcutaneous administration.
Figure 6:
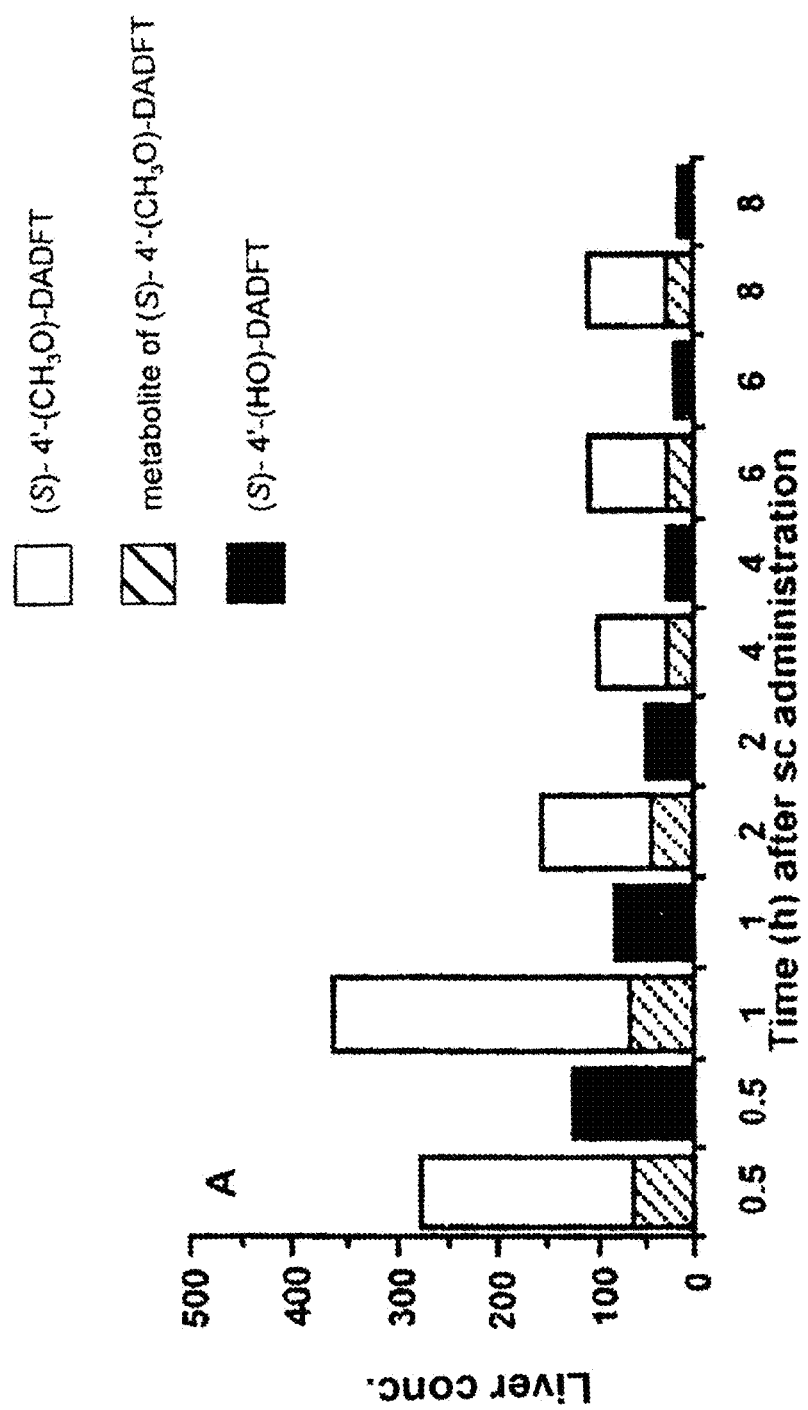
FIG. 6 shows the distribution of (S)-4'-(HO)-DADFT and (S)-4'-($CH_3$O)-DADFT in the liver of rodents over time following subcutaneous administration.
Figure 7:
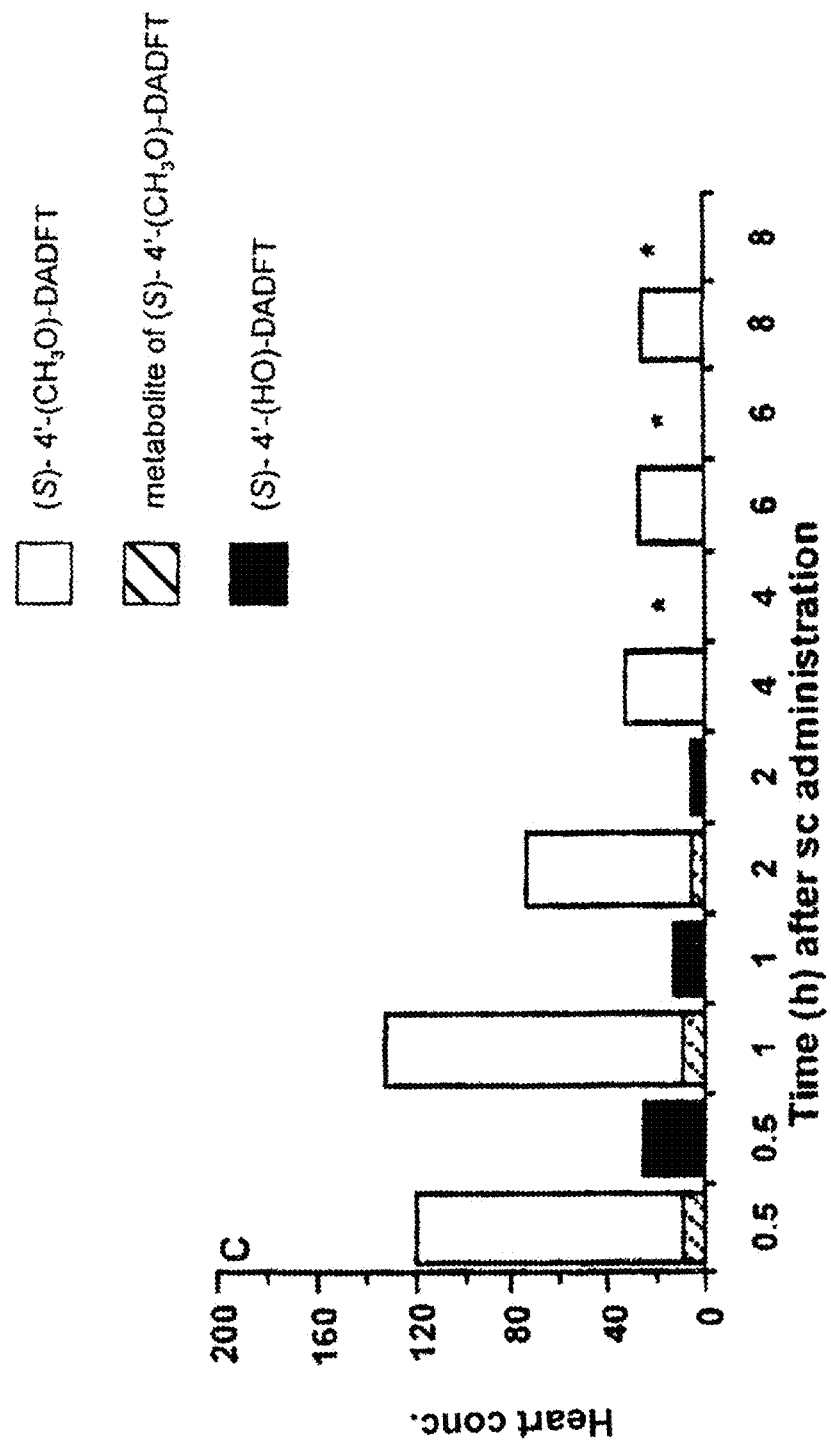
FIG. 7 shows the distribution of (S)-4'-(HO)-DADFT and (S)-4'-($CH_3$O)-DADFT in the heart of rodents over time following subcutaneous administration.
Figure 8:
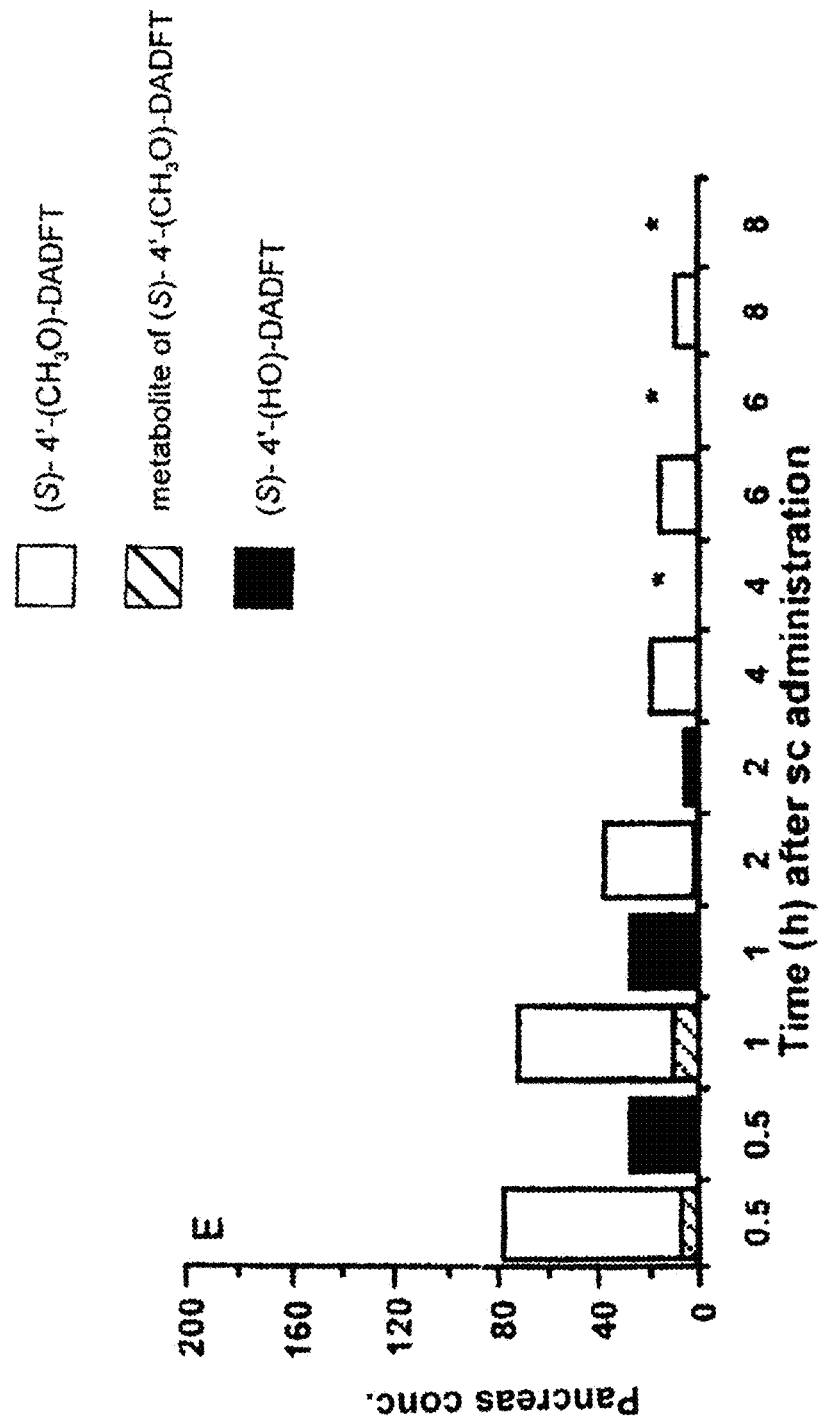
FIG. 8 shows the distribution of (S)-4'-(HO)-DADFT and (S)-4'-($CH_3$O)-DADFT in the pancreas of rodents over time following subcutaneous administration.

Table 3 and FIG. 2-FIG. 8 show that there is very little metabolism of (S)-4-(HO)-DADFT-PE back to (S)-4-(HO) DADFT (indicated as (metabolite in Table 3 and FIG. 2-FIG. 5) occurring in any tissue. Most of the PE is found in the liver, kidney and pancreas. It is important to note that there is much less of the PE in the kidney that there is of (S)-4-(HO)-DADFT at any time point, (FIG. 2).

Example 5

Uranium Excretion in Rats by Iron Chelators

Figure 9:
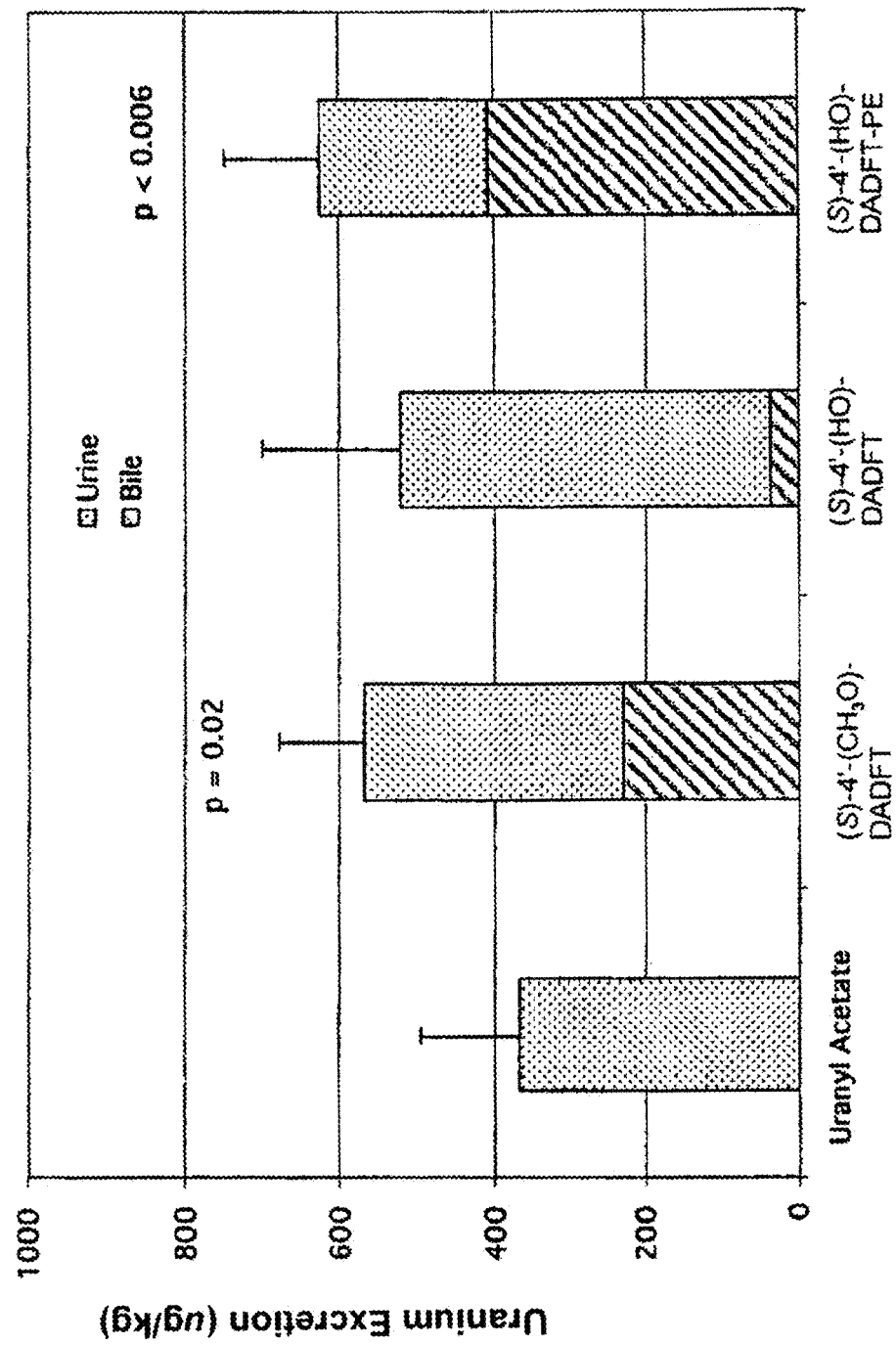
FIG. 9 shows the uranium excretion in rats induced by compounds of the invention following administration.

Male Sprague-Dawley rats averaging 450 g were anesthetized using sodium pentobarbital (55 mg/kg) administered intraperitoneally. The bile duct was cannulated using 22-gauge polyethylene tubing. The rats were given uranyl acetate subcutaneously at 5 mg/kg. Immediately thereafter, the rats were given the chelator intraperitoneally at a dose of 300 μmol/kg. 24-h urine and 24-h bile samples were collected, acidified with 2% concentrated nitric acid and assessed by Inductively Coupled Plasma Mass Spectrometry (ICP-MS) for their uranium content. The results are shown in FIG. 9.

While this invention has been particularly shown and described with references to preferred embodiments thereof, it will be understood by those skilled in the art that various changes in form and details may be made therein without departing from the scope of the invention encompassed by the appended claims.

TABLE 3

Tissue and Plasma Concentrations of (S)-4'-(HO)-DADFT-PE upon sc Administration vs. Concentrations of (S)-4'-(HO)-DADFT upon sc Administration of (S)-4'-(HO)-DADFT[a]

| Administered cmpd | Time (h) | (S)-4'-(HO)-DADFT-PE | | (S)-4'-(HO)-DADFT | | (S)-4'-(CH$_3$O)-DADFT | |
|---|---|---|---|---|---|---|---|
| | | (S)-4'-(HO)-DADFT-PE (metabolite) | (S)-4'-(HO)-DADFT-PE | DADFT (S)-4'-(HO)-DADFT | (S)-4'-(CH$_3$O)-DADFT (metaboolite) | (S)-4'-(CH$_3$O)-DADFT | |
| Liver | 2 | 2.8 ± 0.1 | 131.6 ± 32.2 | 48.3 ± 20.3 | 43.5 ± 4.5 | 111.0 ± 14.0 | |
| | 4 | 0.0 ± 0.0 | 66.9 ± 12.4 | 25.0 ± 3.9 | 24.6 ± 1.1 | 73.8 ± 10.8 | |
| | 6 | 0.0 ± 0.0 | 34.3 ± 1.5 | 19.3 ± 2.0 | 26.9 ± 5.1 | 80.9 ± 10.7 | |
| | 8 | 0.0 ± 0.0 | 25.4 ± 4.6 | 12.3 ± 0.8 | 25.0 ± 3.6 | 81.4 ± 15.9 | |
| Kidney | 2 | 0.0 ± 0.0 | 41.1 ± 3.0 | 97.1 ± .50 | 49.9 ± 21.3 | 97.5 ± 24.5 | |
| | 4 | 0.0 ± 0.0 | 33.7 ± 13.5 | 26.6 ± 7.1 | 23.2 ± 1.7 | 57.0 ± 15.5 | |
| | 6 | 0.0 ± 0.0 | 13.7 ± 2.1 | 13.0 ± 8.0 | 21.7 ± 6.2 | 67.2 ± 9.9 | |
| | 8 | 0.0 ± 0.0 | 7.4 ± 2.1 | 8.8 ± 2.9 | 25.3 ± 2.5 | 67.4 ± 19.9 | |
| Heart | 2 | 0.0 ± 0.0 | 9.2 ± 2.6 | 4.6 ± 3 | 6.4 ± 0.6 | 66.2 ± 2.2 | |
| | 4 | 0.0 ± 0.0 | 5.3 ± 1.4 | 0 ± 0 | <4.8 | 32.6 ± 3.6 | |
| | 6 | 0.0 ± 0.0 | 0.0 ± 0.0 | 0 ± 0 | <4.8 | 28.2 ± 0.7 | |
| | 8 | 0.0 ± 0.0 | 2.0 ± 1.7 | 0 ± 0 | <4.8 | 26.3 ± 9.7 | |
| Pancreas | 2 | 0.0 ± 0.0 | 29.6 ± 24.8 | 5.8 ± 1.3 | 1.3 ± 2.2 | 37.1 ± 3.8 | |
| | 4 | 0.0 ± 0.0 | 12.6 ± 5.2 | 0 ± 0 | 0.0 ± 0.0 | 19.4 ± 1.4 | |
| | 6 | 0.0 ± 0.0 | 4.6 ± 1.6 | 0 ± 0 | 0.0 ± 0.0 | 16.5 ± 4.5 | |
| | 8 | 0.0 ± 0.0 | 2.7 ± 2.6 | 0 ± 0 | 0.0 ± 0.0 | 9.7 ± 0.7 | |
| Brain | 2 | 0.0 ± 0.0 | 0.5 ± 0.9 | 0 ± 0 | <2.4 | 13.2 ± 4.8 | |
| | 4 | 0.0 ± 0.0 | 0.0 ± 0.0 | 0 ± 0 | <2.4 | 7.4 ± 0.7 | |
| | 6 | 0.0 ± 0.0 | 0.0 ± 0.0 | 0 ± 0 | <2.4 | 4.8 ± 3.1 | |
| | 8 | 0.0 ± 0.0 | 0.0 ± 0.0 | 0 ± 0 | <2.4 | <1.6 ± 0.0 | |
| Plasma | 2 | 2.7 ± 0.3 | 16.2 ± 4.2 | 13.1 ± 2.7 | 8.4 ± 1.8 | 478.8 ± 36.8 | |
| | 4 | 2.2 ± 0.6 | 5.3 ± 2.6 | 2 ± 0.4 | 4.2 ± 1.0 | 236.3 ± 42.0 | |
| | 6 | 2.3 ± 0.3 | 1.0 ± 1.0 | 0 ± 0 | 1.8 ± 0.6 | 142.5 ± 29.5 | |
| | 8 | 1.2 ± 0.1 | 0.0 ± 0.0 | 0 ± 0 | 0.0 ± 0.0 | 79.6 ± 13.3 | |

[a]Reported as nmol/g wet wt (tissue) or μM (plasma), mean ± SD for 3 animals per time point.

What is claimed is:

1. A method of treating transfusional iron overload in a subject, comprising administering to the subject a therapeutically or prophylactically effective amount of a compound of the formula:

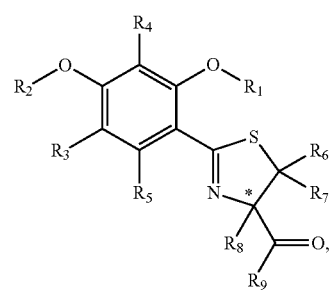
(I)

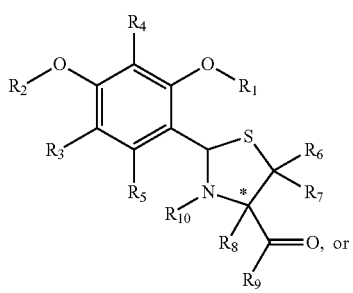
(II)

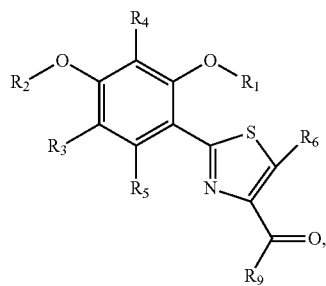
(III)

wherein:
R$_1$ is —H or an acyl group;
R$_2$ is —[(CH$_2$)$_n$—O]$_x$—[(CH$_2$)$_n$—O]$_y$—R';
R$_3$, R$_4$ and R$_5$ are each independently —H, an alkyl group, or —OR$_{11}$;
R$_6$, R$_7$, and R$_8$ are each independently —H or an alkyl group;
R$_9$ is —OR$_{12}$ or —N(OH)R$_{13}$;
R$_{10}$ is —H or an alkyl group;
R$_{11}$ is —H, an alkyl group or an acyl group;
R$_{12}$ is —H or an alkyl group;
R$_{13}$ is an alkyl group,

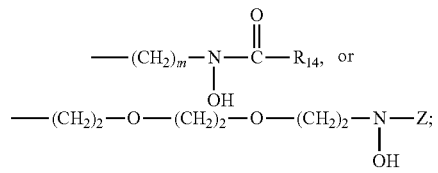

R$_{14}$ is an alkyl group;
R' is an alkyl group;
m is an integer from 1 to 8;
each n is independently an integer from 1 to 8;
x is an integer from 1 to 8;
y is an integer from 0 to 8;
Z is —C(O)R$_{14}$,

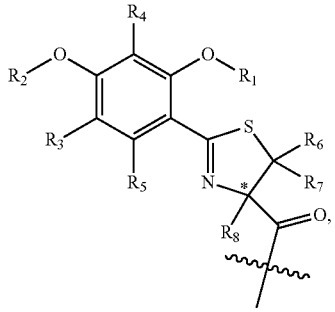

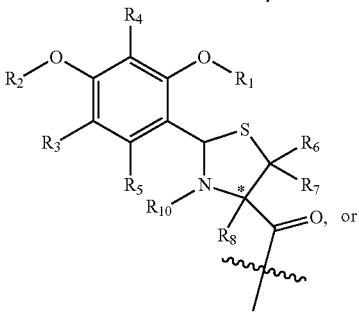

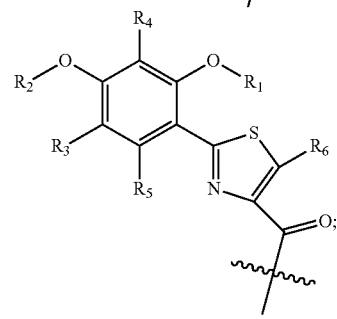

or a pharmaceutically acceptable salt thereof.

2. The method of claim 1, wherein the compound is of Formula (I):

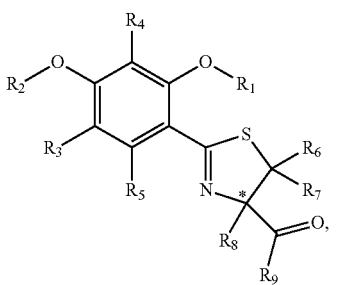
(I)

or a pharmaceutically acceptable salt thereof.

3. The method of claim 2, wherein R$_9$ is —OR$_{12}$; R$_8$ is —H or —CH$_3$; R$_6$ and R$_7$ are independently —H or —CH$_3$; and R$_3$, R$_4$, and R$_5$ are each —H.

4. The method of claim 3, wherein R$_2$ is —[(CH$_2$)$_n$—O]$_x$—R'; n is 1 to 4; and x is 1 to 4.

5. The method of claim 1, wherein the compound is of the formula:

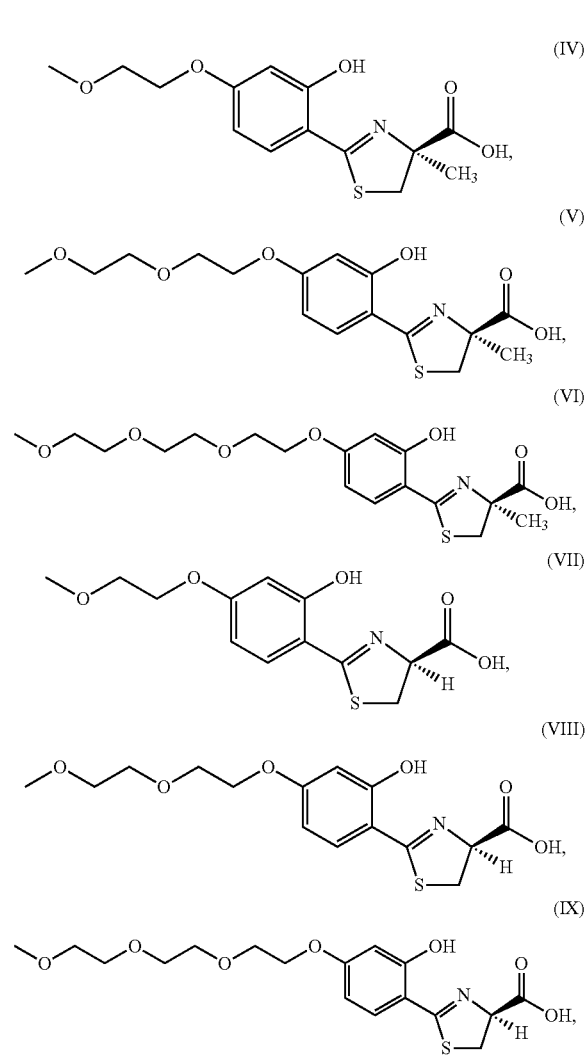

or a pharmaceutically acceptable salt of any of the foregoing.

6. A method of treating transfusional iron overload in a subject, comprising administering to the subject a therapeutically or prophylactically effective amount of a compound of Formula (VI):

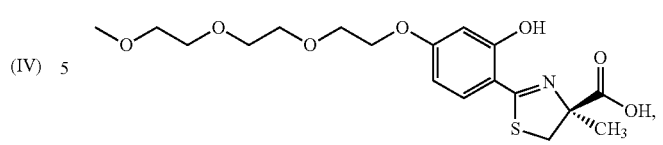

or a pharmaceutically acceptable salt thereof.

7. The method of claim 2, wherein carbon atom labeled with "*" is of the S-configuration.

8. The method of claim 2, wherein carbon atom labeled with "*" is of the R-configuration.

9. The method of claim 1, wherein $R_9$ is $-OR_{12}$.

10. The method of claim 9, wherein $R_8$ is —H.

11. The method of claim 9, wherein $R_8$ is $-CH_3$.

12. The method of claim 9, wherein $R_6$ and $R_7$ are —H.

13. The method of claim 9, wherein $R_6$ and $R_7$ are $-CH_3$.

14. The method of claim 9, wherein $R_3$, $R_4$, and $R_5$ are —H.

15. The method of claim 9, wherein $R_2$ is $-[(CH_2)_n-O]_x-R'$; n is independently 1 to 4; and x is 1 to 4.

16. The method of claim 9, wherein $R_1$ is —H.

17. The method of claim 1, wherein the pharmaceutically acceptable salt is an alkali metal salt or alkaline earth metal salt.

18. The method of claim 1, wherein the pharmaceutically acceptable salt is a sodium salt, potassium salt, magnesium salt, or calcium salt.

19. The method of claim 6, wherein the pharmaceutically acceptable salt is an alkali metal salt or alkaline earth metal salt.

20. The method of claim 6, wherein the pharmaceutically acceptable salt is a sodium salt, potassium salt, magnesium salt, or calcium salt.

21. The method of claim 9, wherein $R_{12}$ is —H.

22. The method of claim 9, wherein $R_{12}$ is an alkyl group.

23. The method of claim 9, wherein $R_{12}$ is a $C_{1-6}$ alkyl group.

24. The method of claim 1, wherein each n is 2.

25. The method of claim 1 comprising administering to the subject a therapeutically effective amount of the compound.

26. The method of claim 6 comprising administering to the subject a therapeutically effective amount of the compound.

* * * * *